United States Patent [19]

Bar-Shalom et al.

[11] Patent Number: 5,213,808
[45] Date of Patent: May 25, 1993

[54] CONTROLLED RELEASE ARTICLE WITH PULSATILE RELEASE

[75] Inventors: Daniel Bar-Shalom, Kokkedal; Kindt-Larsen, Vedbaek, both of Denmark

[73] Assignee: Buhk Meditec A/A, Hellerup, Denmark

[21] Appl. No.: 505,924

[22] Filed: Apr. 6, 1990

[30] Foreign Application Priority Data

Sep. 22, 1989 [DK] Denmark ............... 4699/89

[51] Int. Cl.⁵ ............................... A61K 9/24
[52] U.S. Cl. ................... 424/473; 424/485; 424/488
[58] Field of Search ............ 424/485, 488, 473

[56] References Cited

U.S. PATENT DOCUMENTS

| | | | |
|---|---|---|---|
| 3,634,584 | 1/1972 | Poole | 424/469 |
| 4,177,256 | 12/1979 | Michaels et al. | 424/22 |
| 4,182,330 | 1/1980 | Michaels | 128/260 |
| 4,343,789 | 8/1982 | Kawata et al. | 424/78 |
| 4,359,483 | 11/1982 | Kaetsu | 427/2 |
| 4,486,471 | 12/1984 | Samejima | 427/213.3 |
| 4,576,604 | 3/1986 | Guittard et al. | 604/890 |
| 4,629,261 | 12/1986 | Snipes | 424/19 |
| 4,673,405 | 6/1987 | Guittard et al. | 604/890 |
| 4,723,958 | 2/1988 | Pope et al. | 604/890.1 |
| 4,744,074 | 9/1988 | Snipes | 424/19 |
| 4,744,976 | 5/1988 | Snipes | 424/408 |
| 4,806,337 | 2/1989 | Snipes et al. | 71/65 |
| 4,810,502 | 3/1989 | Ayer et al. | 424/473 |
| 5,023,088 | 6/1991 | Wong | 424/473 |

FOREIGN PATENT DOCUMENTS

| | | |
|---|---|---|
| 103387 | 8/1983 | European Pat. Off. |
| 117164 | 1/1984 | European Pat. Off. |
| 132384 | 7/1984 | European Pat. Off. |
| 199362 | 4/1986 | European Pat. Off. |
| 230654 | 12/1986 | European Pat. Off. |
| 232877 | 2/1987 | European Pat. Off. |
| 1-10622 | 4/1989 | Japan . |
| 2160100 | 6/1985 | United Kingdom . |
| 2189995 | 4/1987 | United Kingdom . |
| WO8904673 | 6/1989 | World Int. Prop. O. |

*Primary Examiner*—Thurman K. Page
*Assistant Examiner*—D. Gabrielle Phelan
*Attorney, Agent, or Firm*—Foley & Lardner

[57] ABSTRACT

An article for controlled delivery of an active substance into an aqueous phase has a first layer containing an active substance, and a second layer of a crystalline polymer matrix and a non-ionic surface active agent, the second layer also containing the same or different active substance substantially homogeneously dispersed therein. The article enables release of a drug at a constant plateau level, followed by a pulse of drug after a predetermined time, thus making the composition of the invention especially suitable for use in, e.g., treatment of rheumatoid arthritis or related disorders with non-steroidal anti-inflammatory agents.

36 Claims, 5 Drawing Sheets

CONTROLLED RELEASE ARTICLE WITH PULSATILE RELEASE

BACKGROUND OF THE INVENTION

All controlled release pharmaceutical products have in common the goal of improving drug therapy over that achieved with their non-controlled counterparts. Ideally, the use of an optimally designed controlled release preparation in medical treatment is characterized by a minimum of drug substance being employed to cure or control the condition in a minimum amount of time.

In general, a controlled release preparation is a pharmaceutical composition capable of releasing the active substance at the required rate to maintain a constant pharmacological activity for some desirable period of time. Such dosage forms provide a supply of a drug to the body during a predetermined period of time and thus maintain drug levels in the therapeutic range for longer periods of time than conventional non-controlled formulations.

Drug levels can be maintained in the therapeutic range for longer periods of time by giving larger doses of conventionally formulated dosage forms. However, this is not usually a suitable approach, as such doses may produce toxic drug levels. Alternatively, another approach is to administer a drug at frequent intervals of time, resulting in oscillating drug levels, the so-called peak and valley effect. This approach is generally associated with several potential problems, such as a large peak (toxic effect) and valley (non-active drug level) effect, and a lack of patient compliance leading to drug therapy inefficiency or failure.

Controlled release preparations may be designed to rapidly release a predetermined fraction of the total drug dose. This loading dose is an amount of a drug which will provide a desired pharmacological response as promptly as is possible according to the biopharmaceutical properties of the drug. Such formulations which initially release a burst of a therapeutic agent and then release the agent at an essentially constant rate are known e.g. from EP Patent Application No. 103,387. EP Patent Application No. 117.164 and U.S. Pat. No 4.576,604.

The above-mentioned controlled release preparations are long-acting and release the drug in a sustained manner. However, these types of formulations may result in an undesirable decreased bioavailability, and furthermore, the maintenance of the therapeutic drug level in an organism for a prolonged period of time may lead to the development of tolerance and chronic toxicity.

In the case of sustained release or long-acting preparations, the active substance is continuously and slowly released from the preparation at a constant and controlled rate. However, it is impossible to interrupt the release of active substance from such preparations, i.e. to release it at timed intervals.

It has, however, recently been accepted that a certain fluctuation in the drug level is beneficial in the treatment of various diseases in which circadian rhythm or biorhythm effects may influence the condition being treated. For instance, some physiologically active substances are periodically produced in vivo at certain time intervals, and it may accordingly be desirable to administer such substances in a dosage form which periodically releases the active substance at predetermined time intervals. An appropriate dosage regimen will then lead to a response which is specifically directed to the needs of the particular condition being treated.

Various repeat action formulations are known e.g. Spansuls®, wherein up to four dosage units may be employed in each tablet. Each dosage unit will then be released over predetermined intervals of time depending on the drug properties and manufacturing process. Repeat action formulations may be obtained by coating individual particles or granules of a drug with varying thicknesses of a slowly soluble coating material. The time required for dissolution of the coating is a function of the coating thickness and dissolution rate of the coating substance.

Other drug delivery systems for controlled release of an active substance in discrete pulses are described in. e.g., EP Patent Application Nos. 132,384, 199,362 and 246,819, in GB Patent Application No. 2,189,995 and in JP Patent Application No. 110622/1989. The systems described in these applications include hydrogels, osmotic systems, liposomes and multilayer tablets. Release of the active substance is essentially based on diffusion of the substance through the formulation or on differences in osmotic pressure between an internal layer of the preparation and the surrounding medium.

These pulsatile release formulations have several drawbacks. For example, a strictly controlled release of an active substance from liposomes is difficult to achieve due to, e.g., physical stability problems related to the liposome formulation. Furthermore, the osmotic systems have recently been shown to possess undesirable side effects after oral administration to humans.

SUMMARY OF THE INVENTION

It has now been found that it is possible to prepare a novel controlled release composition which provides a precisely regulated non-initial burst release of an active substance at a predetermined time, and which is free of the drawbacks which may be associated with known art controlled release compositions. The composition may in addition optionally provide a controlled and constant release of the same or a different active substance embedded in a matrix layer.

The composition of the invention is suitable for the treatment of conditions where the active substance advantageously is to be delivered at a predetermined time of at least about 15 minutes after administration.

Delayed absorption is of particular relevance when the absorption of the active substance is limited to or proceeds substantially better in a certain area, e.g. in the gastrointestinal tract. Such drugs with a narrow absorption window include e.g. captopril, amino acids, vitamins, minerals, and peptides. The release of the drug from the composition of the invention will occur at a predetermined time which in such cases typically is about 1-12 hours.

Delayed absorption of an active substance may also be desirable in connection with the treatment of diseases in which circadian rhythm or biorhythm effects can influence the condition being treated, or when an effective therapy is desired in the early morning before awakening. Such active substances comprise sex hormones, anti sex hormones, antimigraine agents, cardiovascular agents, including agents against essential hypertension and orthostatic hypotension, coronary dilators, antiasthma agents, diuretics, antiinflammatory agents, analgesics, and steroid and anticancer agents, including a combination of methotrexate and leucovorine. In such cases, release of the active substance will typically take place about 6-10 hours after administration.

Delayed release of an active substance is furthermore important in the treatment of diseases localized to the small intestine or the colon. Such diseases are often treated by the oral route of administration and the therapy suffers from several drawbacks which are mainly due to a non-specific absorption along the gastrointestinal tract. Consequently, in order to obtain effective concentrations of the drug at the diseased site high doses have to be given, which in turn lead to severe local as well as systemic side effects. Delayed release will in such cases lead to a localized drug action at the specific disease sites without additional side effects. Release of the active substance solely in the colon, for example, requires a composition comprising an outer layer B) without an active substance, the layer being completely eroded about 6-20 hours after administration.

Accordingly, the present invention relates to a composition for controlled delivery of at least one active substance into an aqueous phase by erosion at a substantially constant rate of a surface or surfaces of the composition, the composition comprising at least one layer of A) at least one active substance and
optionally, at least one filler, the active substance(s) being substantially homogeneously dispersed therein, and at least one layer of one of the following:

B) a matrix of a substantially water soluble crystalline polymer or a mixture of substantially water soluble crystalline polymers,
a water dispersible or water soluble surface active agent or a mixture of such surface active agents dispersed in the crystalline polymer phase in an amount of 0-50% by weight of the crystalline polymer and surface active agent, the surface active agent comprising a compound or compounds having at least one domain which is compatible with the crystalline polymer phase and at least one other domain which is substantially lipophilic, and having a melting point which is lower than that of the crystalline polymer,
optionally, a filler, and C) at least one active substance substantially homogeneously dispersed in a matrix comprising
a substantially water soluble crystalline polymer or a mixture of substantially water soluble crystalline polymers,
a water dispersible or water soluble surface active agent or a mixture of such surface active agents dispersed in the crystalline polymer phase in an amount of 0-50% by weight of the crystalline polymer and surface active agent, the surface active agent comprising a compound or compounds having at least one domain which is compatible with the crystalline polymer phase and at least one other domain which is substantially lipophilic, and having a melting point which is lower than that of the crystalline polymer, and
optionally, a filler, the composition optionally being provided with a coating having at least one opening exposing at least one of the layers A), B) or C) to the aqueous phase, the surface active agent in the matrix of layers B) and C) having a function as a repair medium reducing the water affinity of domains between grains and in cracks in the crystalline polymer matrix and in the crystalline polymer matrix itself thereby substantially eliminating water diffusion in the interface between the polymer crystals and thus substantially limiting diffusion of water into the composition to the surface layer of the matrix, so that erosion of the matrices of layers B) and C) is predominantly effected by the dissolving action of the aqueous phase on a surface or surfaces of the composition exposed to the aqueous phase and takes place at a substantially constant and pH-independent rate, the composition being adapted so that at least one layer B) or C) becomes exposed to the aqueous phase upon administration of the composition, said layer having a thickness which allows at least one remote layer A) comprising an active substance to become exposed to the aqueous phase after a predetermined period of at least about 15 minutes after administration of the composition.

The composition of the invention is especially suitable for use in, for example, the treatment of rheumatoid arthritis or related disorders with non-steroidal anti-inflammatory agents, where conventional or hitherto known, controlled release formulations are not able to release a sufficient amount of the active drug at the time analgesia is needed, whereby an insufficient drug level is achieved in the blood. The composition according to the invention enables release of the correct amount of drug at a predetermined time e.g. in the morning before waking, when untreated morning stiffness caused by a dramatic change in posture leads to an intense feeling of pain for arthritis sufferers.

In order to obtain a strictly controlled erosion of matrix layers B) and/or C), these matrices must be substantially impenetrable to aqueous phases present where the composition of the invention is introduced into the body (e.g. in the gastrointestinal tract, including the rectum or in the vagina) or into a body cavity via a catheter (e.g. the urinary bladder, kidney pelvis, the gall bladder, the uterus, a central nervous system cavity, infectious/malignant/post-operative cavities, etc.). A strictly controlled and reproducible erosion of the matrix layer is a prerequisite for obtaining a strictly controlled release rate of the active substance. This is obtained by limiting the action of water to the surface(s) of the matrix. As the aqueous phases can only act on the surfaces of the composition, the active substance present in layer A) and optionally embedded in layer C) and is only exposed and released to the aqueous phases in question when it is present at the surface of matrix layer B) or the matrix B) or C) is eroded, leaving layer A) susceptible to the action of water.

The inclusion of an active substance in a composition into which water diffusion is substantially eliminated will furthermore impart stability to the composition, so that the active substance will remain intact and active even when the composition has been exposed to aqueous phases for a predetermined time. Most labile drug substances are degraded by hydrolysis, i.e. by the influence of water. Prior to hydrolysis, the drug must interact with an aqueous phase. As the active substance embedded in the composition according to the invention is only available to an aqueous phase when released or immediately prior to its release from the composition, hydrolysis of the active substance will only take place at the time in which the drug is released. Such a composition will therefore ensure the stability of the active substance for the entire period of time the composition is present in the aqueous phase.

Due to the nature of the composition of the invention, it is possible to obtain a substantially controlled pulsatile release, optionally in combination with a constant rate of release of the active substance over a specific period of time, corresponding to the dosage necessary for the treatment in question, so that adherence to a strict dosage regimen, e.g. requiring administration of a drug at set intervals up to several times a day, may be dispensed with. It is possible to combine two or more active substances, each following an independent release pattern; however the release pattern of such substances may also be identical.

An additional advantage of the composition of the invention, compared to other known controlled release compositions, is that it may be produced by relatively simple and inexpensive methods, e.g. by extrusion or injection molding, as will be explained in more detail below. Furthermore, the composition according to the invention allows for the incorporation of high concentrations of the active substance relative to the composition's size. This is obviously a great advantage, since it allows for the delivery of the required amount of the active substance without the composition being unnecessarily large. In addition, sparingly soluble or non-soluble active substances, which can otherwise be difficult to administer, may be readily incorporated into the composition of the invention, since such substances are compatible with the lipophilic domains of the surface active agent.

The present invention also relates to a method for preparing the above-mentioned composition. Thus, the invention further relates to a method for preparing a composition for controlled delivery of at least one active substance into an aqueous phase by erosion at a substantially constant rate of a surface or surfaces of the composition, the method comprising forming at least one layer of A) at least one active substance and
  optionally, at least one filler the active substance(s) being substantially homogeneously dispersed therein, and at least one layer of one of the following:

B) a matrix of a substantially water soluble crystalline polymer or a mixture of substantially water soluble crystalline polymers,
  a water dispersible or water soluble surface active agent or a mixture of such surface active agents dispersed in the crystalline polymer phase in an amount of 0-50% by weight of the crystalline polymer and surface active agent, the surface active agent comprising a compound or compounds having at least one domain which is compatible with the crystalline polymer phase and at least one other domain which is substantially lipophilic, and having a melting point which is lower than that of the crystalline polymer,
  optionally, a filler, and C) at least one active substance substantially homogeneously dispersed in a matrix comprising
  a substantially water soluble crystalline polymer or a mixture of substantially water soluble crystalline polymers,
  a water dispersible or water soluble surface active agent or a mixture of such surface active agents dispersed in the crystalline polymer phase in an amount of 0-50% by weight of the crystalline polymer and surface active agent, the surface active agent comprising a compound or compounds having at least one domain which is compatible with the crystalline polymer phase and at least one other domain which is substantially lipophilic, and having a melting point which is lower than that of the crystalline polymer, and
  optionally, a filler, so as to form a layered composition, and optionally providing the composition with coating having at least one opening exposing at least one of the layers B), A) or C) to the aqueous phase, the surface active agent in the matrix of layers B) and C) having a function as a repair medium reducing the water affinity of domains between grains and in cracks in the crystalline polymer matrix and in the crystalline polymer matrix itself, thereby substantially eliminating water diffusion in the interface between the polymer crystals and thus substantially limiting diffusion of water into the composition to the surface layer of the matrix, so that erosion of the matrices of layers B) and C) in an aqueous phase is predominantly effected by the dissolving action of the aqueous phase on a surface or surfaces of the composition exposed to the aqueous phase and takes place at a substantially constant and pH-independent rate, the composition being adapted so that at least one layer B) or C) becomes exposed to the aqueous phase upon administration of the composition, said layer being provided with a thickness which allows at least one remote layer A) comprising an active substance to become exposed to the aqueous phase after a predetermined period of at least about 15 minutes after administration of the composition.

DETAILED DISCLOSURE OF THE INVENTION

The composition of the invention is useful whenever controlled release of an active substance into an aqueous liquid environment is desired. In the following, the term "controlled release" is used to designate a release at a predetermined time and at a desired rate during a predetermined release period.

For each particular type of active substance to be administered and each particular condition to be treated, a particular release pattern is required. The adaptation of the composition to the particular required in vivo release pattern may be performed either on the basis of in vivo experiments or, as it is often preferred, by utilizing standardized in vitro tests where a correlation between in vivo data and in vitro data can be obtained. Suitable in vitro tests may be various standardized dissolution tests as described in e.g. USP XXII. Methods for establishing the correlation between in vitro and in vivo tests will be well known by a person skilled in the art.

The expression "active substance" as used herein broadly includes any compound, or mixture thereof, that can be delivered from the composition to produce a beneficial result. The active and beneficial agents include pesticides, herbicides, germicides, biocides, algicides, rodenticides, fungicides, insecticides, antioxidants, plant growth promoters, plant growth inhibitors, preservatives, disinfectants, sterilization agents, catalysts, chemical reactants, fermentation agents, catalysts, chemical reactants, fermentation agents, food supplements, nutrients cosmetics, pharmaceutically active substances (drugs), vitamins, sex sterilants, fertility inhibitors, fertility promoters, air purifiers, micro-organism attenuators, ecological agents and other agents that benefit the environment in which they are used.

In the present context, the term "drug" includes any physiologically or pharmacologically active substances that produces a localized or systemic effect in animals, in particular mammals, including humans and primates. Other animals include domestic household, sport or farm animals such as sheep, goats, cattle, horses and pigs, laboratory animals such as mice, rats and guinea pigs, fishes, to avians, reptiles and zoo animals. In the present context, the term "ecological agent" denotes a non-pharmaceutical substance which has a biological effect on plants or animals in the environment. An ecological agent may be a pesticide, such as an insecticide or herbicide, a fertilizer, a pheromone, a plant growth hormone, or the like.

The pharmaceutical composition comprises a layer A) of at least one active substance and at least one layer B) or C) comprising a matrix of a substantially water soluble crystalline polymer or a mixture of substantially water soluble crystalline polymers.

Active Substances

The active drug layer may contain as the sole ingredient the active substance alone, but, in general, various fillers are added to improve the bioavailability of the drug or to facilitate the manufacturing process.

The pharmaceutically active substance or substances included in the composition of the invention may be selected from many therapeutic categories, in particular from substances which may advantageously be administered orally, rectally, vaginally, or administered to a body cavity (e.g. the urinary bladder, kidney pelvis, the gall bladder, the uterus, a central nervous system cavity, infectious/malignant/post-operative cavities, etc.). Examples of such substances are hypnotics, sedatives, tranquilizers, anti-convulsants, musclerelaxants, analgesics, anti-inflammatory, anesthetics, anti-spasmodics, anti-ulcer-agents, anti-parasitics, anti-microbials, anti-fungal, cardiovascular agents, diuretics, cytostatics, anti-neoplastic agents, anti-viral agents, anti-glaucoma agents, anti-depressants, sympathomimetics, hypoglycaemics, diagnostic agents, anti-cough, physic energizers, anti-parkinson agents, local anesthetics, muscle contractants, anti-malarials, hormonal agents, contraceptives, anorexic, anti-arthritic, anti-diabetic, anti-hypertensive, anti-pyretic, anti-cholingergic, bronchodilator, central nervous system, inotropic, vasodilator, vasoconstrictor, decongestant, hematinic, electrolyte supplement, germicidal, parasympathetolytic, parasymphatethomimetic, antiemetic, psychostimulant, vitamin, beta-blockers, H-2 blocker, beta-2 agonist, counterirritants, coagulating modifying agents, stimulants, antihormones, drug-antagonists, lipid-regulating agents, uricosurics, cardiac glycosides, ergot and derivatives thereof, expectorants, muscle relaxants, anti-histamines, purgatives, contrastmaterials, radiopharmaceuticals, imaging agents, anti-allergic agents.

Examples of specific active substances are:

Codeine, ethylmorphine, dextromethorphan, noscapine, pentoxiverine, acetylcysteine, bromhexine, epinephrine, isoprenaline, orciprenaline, ephedrine, fenoterol, rimiterol, ipratropium, cholinetheophyllinate, proxiphylline, bechlomethasone, budesonide, deslanoside, digoxine, digitoxin, disopyramide, proscillaridin, chinidine, procainamide, mexiletin, flecainide, alprenolol, proproanolol, nadolol, pindolol, oxprenolol, labetalol, timolol, atenolol, pentaeritrityltetranitrate, isosorbiddinitrate, isosorbidmononitrate, niphedipin, phenylamine, verapamil, diltiazem, cyclandelar, nicotinylalcholhol, inositolnicotinate, alprostatdil, etilephrine, prenalterol, dobutamine, dopamine, dihydroergotamine, guanetidine, betanidine, methyldopa, reserpine, guanfacine, trimethaphan, hydralazine, dihydralazine, prazosine, diazoxid, captopril, nifedipine, enalapril, nitroprusside, bendroflumethiaziede, hydrochlorthiazide, metychlothiazide, polythiazide, chlorthalidon, cinetazon, clopamide, mefruside, metholazone, bumetanide, ethacrynacide, spironolactone, amiloride, chlofibrate, nicotinic acid, nicheritrol, brompheniramine, cinnarizine, dexchlorpheniramine, clemastine, antazoline, cyproheptadine, promethazine, cimetidine, ranitidine, sucralfat, papaverine, moxaverine. atropin, butylscopolamin, emepron, glucopyrron, hyoscyamine, mepensolar, methylscopolamine, oxiphencyclimine, probanteline, terodilin, sennaglycosides, sagradaextract, dantron, bisachodyl, sodiumpicosulfat, etulos, diphenolxylate, loperamide, salazosulfapyridine, pyrvin, mebendazol, dimeticon, ferrofumarate, ferrosuccinate, ferritetrasemisodium, cyanochobalamine, folic acid heparin, heparin co-factor, diculmarole, warfarin, streptokinase, urokinase, factor VIII, factor IX, vitamin K, thiotepa, busulfan, chlorambucil, cyclophosphamid, melfalan, carmustin, mercaptopurin, thioguanin, azathioprin, cytarabin, vinblastin, vinchristin, vindesin, procarbazine, dacarbazine, lomustin, estramustin, teniposide, etoposide, cisplatin, amsachrin, aminogluthetimid, phosphestrol, medroxiprogresterone, hydroxiprogresterone, megesterol, noretisteron, tamoxiphen, ciclosporin, sulfisomidine, bensylpenicillin, phenoxymethylpenicillin, dicloxacillin, cloxacillin, flucloxacillin, ampicillin, amoxicillin, pivampicillin, bacampicillin, piperacillin, mezlocillin, mecillinam, pivmecillinam, cephalotin, cephalexin, cephradin, cephadroxil, cephaclor, cefuroxim, cefotaxim, ceftazidim, cefoxitin, aztreonam, imipenem, cilastatin, tetracycline, lymecycline, demeclocycline, metacycline, oxitetracycline, doxycycline, chloramphenicol, spiramycin, fusidic acid, lincomycin, clindamycin, spectinomycin, rifampicin, amphotericin B, griseofulvin, nystatin, vancomycin, metronidazole, tinidazole, trimethoprim, norfloxacin, salazosulfapyridin, aminosalyl, isoniazid, etambutol, nitrofurantoin, nalidixic acid, metenamine, chloroquin, hydroxichloroquin, tinidazol, ketokonazol, acyclovir, interferon idoxuridin, retinol, tiamin, dexpantenol, pyridoxin, folic acid, ascorbic acid, tokoferol, phytominadion, phenfluramin, corticotropin, tetracosactid, tyrotropin, somatotropin, somatrem, vasopressin, lypressin, desmopressin, oxytocin, chloriongonadotropin, cortison, hydrocortison, fludrocortison, prednison, prednisolon, fluoximesteron, mesterolon, nandrolon, stanozolol, oximetolon, cyproteron, levotyroxin, liotyronin, propylthiouracil, carbimazol, tiamazol, dihydrotachysterol, alfacalcidol, calcitirol, insulin, tolbutamid, chlorpropamid, tolazamid, glipizid, glibenclamid, phenobarbital, methyprylon, pyrityldion, meprobamat, chlordiazepoxid, diazepam, nitrazepam, oxazepam, dikaliumchlorazepat, lorazepam, flunitrazepam, alprazolam, midazolam, hydroxizin, chlomethiazol, propionmazine, alimemazine, chlorpromazine, levomepromazine, acetophenazine, fluphenazine, perphenazine, prochlorperazine, trifluoperazine, dixyrazine, thioridazine, periciazin, chlorprothixene, zuclopentizol, flupentizol, thithixen, haloperidol, trimipramin, opipramol, chlomipramin, desipramin, lofepramin, amitriptylin, nortriptylin, protriptylin, maptrotilin, coffein, cinnarizine, cyclizine, dimenhydinate, meclozine, prometazine, thiethylperazine, metoclopramide, scopolamine, phenobarbital, phenytoine, ethosuximide, primidone, carbamazepine, chlonazepam, orphenadrine, atropine, bensatropine, biperiden, metixene, procylidine, levodopa, bromocriptin, amantadine, ambenon, pyridostigmine, synstigmine, disulfiram, morphine, codeine, pentazocine, buprenorphine, pethidine, phenoperidine phentanyl, methadone, piritramide, dextropropoxyphene, ketobemidone, acetylsalicylic acid, phenazone, phenylbutazone, azapropazone, piroxicam, ergotamine, dihydroergotamine, cyproheptadine, pizitifen, flumedroxon, allopurinol, probenecid, sodiummaurothiomalate, auronofin, penicillamine, estradiol, estradiolvalerianate, estriol, ethinylestradiol, dihydrogesteron, lynestrenol, medroxiprogresterone, noretisterone, cyclophenile, clomiphene, levonorgestrel, mestranol, ornidazol, tinidazol, ekonazol, chlotrimazol, natamycine, miconazole, sulbentin, methylergotamine, dinoprost, dinoproston, gemeprost, bromocriptine, phenylpropanolamine, sodiumchromoglicate, azetazolamide, dichlophenamide, betacarotene, naloxone, calciumfolinate, in particular clonidine, theophylline, dipyradamol, hydrochlorthiazide, scopolamine, indomethacine, furosemide, potassium chloride, morphine, ibuprofen, salbutamol, terbutalin.

The drug can be in various forms, such as uncharged molecules, molecular complexes, a pharmacologically acceptable salt such as a hydrochloride, hydrobromide, sulfate, laurylate, palmitate, phosphate, nitrite, nitrate, borate, acetate, maleate, tartrate, oleate, and salicylate. For acid drugs, salts of metals, amines amino acids or organic cations, quaternary ammonium can be used. Derivatives of drugs such as esters, ethers and amides which have solubility characteristics suitable for use herein can be used alone or mixed with other drugs and after their release from the composition can be converted by enzymes, hydrolyzed by body pH or other metabolic processes to the original form, or to a biologically active form.

The composition is in addition suitable for the delivery of polypeptides, for example hormones such as growth hormones, enzymes such as lipases, proteases, carbohydrates, amylases, lactoferrin, lactoperoxidases, lysozymes, nanoparticles, etc., and antibodies. The composition may also be employed for the delivery of microorganisms, either living, attenuated or dead, for example bacteria e.g. gastrointestinal bacteria such as streptococci, e.g. S. faecium, Bacillus spp. such as *B. subtilis* and *B. licheniformis*, lactobacteria Aspergillus spp., bifidogenic factors, or viruses such as indigenous vira, enterovira, bacteriophages, e.g. as vaccines, and fungi such as baker's yeast, *Saccharomyces cerevisiae* and fungi imperfecti. The composition may also be used for the delivery of active agents in specialized carriers such as liposomes, cyclodextrines, nanoparticles, micelles and fats.

Another use for which the composition of the invention is suited is the delivery of antimicrobial agents to the vagina. Examples of such agents are antifungals, for example imidazole antifungals such as clotrimazole, econazol, ketoconazole and miconazole, polyene antifungal antibiotics such as nystatin, and antiprotozoals such as metronidazole and ornidazole.

A further use for which the composition of the invention is suited is the delivery of active substances to animals. Examples of such active substances for veterinary use are antiparasitics, corticosteroids, antibiotics, antiinflammatory agents, growth promoters and permittants, antifungals and antihelmintics.

The active substance included in the composition may be in solid form or dissolved in one of the layers A) and/or C).

An active substance to be administered by the composition of the invention in the form of a solid powder will suitably have a particle size of from about 0.1 $\mu$m to about 500 $\mu$m, typically from about 0.5 $\mu$m to about 300 $\mu$m, more typically from about 1 $\mu$m to about 200 $\mu$m, especially from about 3 $\mu$m to about 100 $\mu$m.

Fillers

The fillers used in combination with the active substance in layer A) may be selected from conventional tablet or capsule excipients. These excipients may be, for example, diluents such as dicalcium phosphate, calcium sulfate, lactose or sucrose or other disaccharides, cellulose, cellulose derivatives, kaolin, mannitol, dry starch, glucose or other monosaccharides, dextrin or other polysaccharides, sorbitol, inositol or mixtures thereof; binders such as acacia, sodium alginate, starch, gelatin, saccharides (including glucose, sucrose, dextrose and lactose), molasses, extract of Irish moss, panwar gum, ghatti gum, mucilage of isapol husk, carboxymethylcellulose, methylcellulose, veegum, larch arabolactan, polyethylene glycols, ethylcellulose, water, alcohols, waxes, polyvinylpyrrolidone or mixtures thereof; lubricants such as talc, magnesium stearate calcium stearate, stearic acid, hydrogenated vegetable oils, sodium benzoate, sodium chloride, leucine carbowax 4000, magnesium lauryl sulfate, colloidal silicon dioxide and mixtures thereof; disintegrants such as starches, clays, cellulose derivatives including croscarmellose, gums, algins, various combinations of hydrogencarbonates with weak acids (e.g. sodium hydrogencarbonate/tartaric acid or citric acid) crospovidone, sodium starch glycolate, agar, cation exchange resins, citrus pulp, veegum HV, natural sponge, bentonite or mixtures thereof; volatile solvents such as alcohols, including aqueous alcohols, petroleum benzine, acetone, ether or mixtures thereof; plasticizers such as sorbitol and glycerine; and others such as cocoa butter, polyethylene glycols, e.g. with a molecular weight of about 1,000–500,000 daltons, typically about 1,000–100,000 daltons, more typically 1,000–50,000 daltons, especially about 1,000–10,000 daltons, in particular about 1,500–5,000 daltons, and mixtures thereof, hydrogenated vegetable oils, glycerinated gelatin or mixtures thereof. Furthermore, the compositions may comprise one or more agents selected from the group consisting of sweetening agents, flavouring agents and colouring agents, in order to provide an elegant and palatable preparation. Examples of colouring agents are water soluble FD&C dyes and mixtures thereof with corresponding lakes and direct compression sugars such as Di-Pac from Amstar. In addition, coloured dye migration inhibitors such as tragacanth, acacia or attapulgite talc may be added.

Matrix

The crystalline polymer matrix typically comprises a polyglycol e.g. in the form of a homopolymer and/or copolymer. Preferred polymers are polyethylene glycols and/or block copolymers of ethylene oxide and propylene oxide. Polyethylene glycols which are suitable for use in the crystalline polymer matrix are those having a molecular weight of from about 10,000 to about 500,000 daltons, typically from about 15,000 to about 300,000 daltons, more typically from about 20,000 to about 300,000 daltons, and especially from about 25,000 to about 200,000 daltons, in particular from about 30,000 to about 150,000. A preferred polyethylene glycol is one which has a molecular weight of about 35,000 daltons. Typical block copolymers may be comprised of up to about 30% by weight of the polypropylene oxide based block, and have a molecular weight of above about 5000 daltons, typically about 5000 to about 30,000 daltons, more typically about 8000 to about 15,000 daltons.

Molecular Weight

Polyethylene glycols are mixtures of condensation polymers of ethylene glycol. The polymers have the general formula $H(OCH_2CH_2)_nOH$ where n is greater than or equal to 4. In general each PEG is followed by a number which corresponds to its average molecular weight.

The average molecular weight (MW) can be calculated from the following equation:

$$MW = \frac{56,110 \times 2}{\text{hydroxyl number}}$$

where the hydroxyl number is defined as the number indicating the amount in mg of potassium hydroxide which is equivalent to the acetic acid which, by acetylation, is bound by 1 g of a substance (cf. Ph.Nord 63, Vol 1, p. 94).

Mixtures of PEG with different average molecular weights can be used in order to obtain a PEG with a desirable average molecular weight. It is important to note that in such cases it is necessary to use the two PEGs which have a MW closest to the desired molecular weight. The individual amount of the two PEGs necessary to obtain a PEG with a desired MW can be calculated from the hydroxyl number and the equation given above.

The crystalline polymer matrix must have a melting point which is above the body temperature of the human or animal in which the composition of the invention is to be used. Thus, the polymer(s) employed in the matrix will suitably have a melting point of about 20°–120° C., typically about 30°–100° C., more typically about 40°–80° C., depending on the how the composition is to be employed.

Surface Active Agents

The matrix layers 8) and/or C) comprising a substantially water soluble crystalline polymer or a mixture of substantially water soluble crystalline polymers include, in addition, a surface active agent substantially homogeneously dispersed in the crystalline polymer phase.

A surface active agent is a compound that can reduce the interfacial tension between two immiscible phases and this is due to the molecule containing two localized regions, one being hydrophilic in nature and the other being hydrophobic.

The surface active agent is water dispersible or water soluble and comprises a compound or compounds having at least one domain which is compatible with the crystalline polymer phase and at least one other domain which is substantially lipophilic. The term "compatible", as used in the context of the invention, refers to the fact that the surface active agent is able to become dispersed in the melted polymer, as explained below. The surface active agent functions primarily as a repair medium in that it has a substantially hydrophilic domain which gives it an affinity to the crystalline polymer phase, thereby filling in domains between grains and in cracks in the crystalline polymer matrix and reducing the water affinity of these domains and in the crystalline polymer matrix itself. Water diffusion in the interface between the polymer crystals is thereby substantially eliminated, thus substantially limiting diffusion of water into the composition to the surface layer of the matrix, so that erosion of the matrices of layers B) and C) is predominantly effected by the dissolving action of the aqueous phase on a surface or surfaces of the composition exposed to the aqueous phase and takes place at a substantially constant and pH-independent rate. As a controlled rate of erosion is a prerequisite for a controlled release of the active substance the repair medium has a very important function, ensuring that a constant surface area is exposed to the aqueous phases during the entire release period.

The above-mentioned cracks and grains in the crystalline polymer matrix are a result of the process in which the crystals are formed. During the crystallization process, the matrix shrinks and tends to form cracks and imperfect zones between the crystal grains. In order to retain its function as a repair medium, the surface active agent should be mobile after the polymer material of the matrix has solidified and the crystals have been formed. Therefore, the melting point of the surface active agent must be lower than that of the crystalline polymer phase.

In order for the surface active agent to function properly as a repair medium for the cracks and grains in the matrix, it is further necessary that a substantially homogeneous distribution of the surface active agent can be obtained in the melted polymer prior to crystallization. Thus, the surface active agent must be capable of becoming dispersed in the melted polymer.

The homogenity of dispersion of the surface active agent in the matrix seems to be important for the erosion rate of the matrix, a more homogeneous dispersion resulting in a slower erosion rate. It is believed that substantially hydrophobic active substances in layer C) tend to lead to a more homogeneous dispersion of the surface active agent, thereby leading to a decreased erosion rate of the matrix, while non-hydrophobic active substances have the opposite effect.

Substantially hydrophilic or water-soluble active substances have been shown to have the opposite effect, i.e. they tend to result in a faster erosion of the matrix. It has furthermore been found that the erosion rate of the crystalline polymer matrix of layers B) and/or C) depends on the molecular weight of the particular crystalline polymer(s) used. Thus, the use of a crystalline polymer with a higher molecular weight will, all other things being equal, lead to a slower erosion rate. The erosion rate of the matrix of layers B) and/or C) is of course also dependent upon the type and amount of surface active agent, as well as the type and amount of any fillers and active substances in the matrix layer.

The surface active agent is typically a non-ionic surfactant. A non-ionic surface active agent is an agent in which the proportions of hydrophilic and hydrophobic groups are substantiall evenly balanced. Thus, they do not ionise to any great extent in solution and they are generally compatible with both anionic and cationic substances.

The hydrophobic groups of the non-ionic surface active agents comprise one or more fatty acid esters and/or fatty alcohol ethers, for example a fatty acid ester and/or fatty alcohol ether having carbon chains of from 12 to 24 carbon atoms, typically from 12 to 20 carbon atoms, such as an ester of palmitic acid or stearic acid or an ether of palmitic alcohol, stearic alcohol, cetyl alcohol, cetostearyl alcohol or wool alcohols. The hydrophilic groups of the non-ionic surface active agents may comprise a polyglycol ester or ether, a polyethylene glycol ester or ether, a polyhydroxy ester or ether and/or a sugar ester or ether such as a sorbitan ester or ether. The surface active agent will suitably have an HLB (hydrophilic-lipophilic balance) value of from about 5 to about 16, typically about 8-15, especially about 9-13. Furthermore, the surface active agent is preferable an agent which is approved for use in products to be ingested by humans or animals, i.e. pharmaceuticals and/or foodstuffs. A preferred surface active agent is polyethylene glycol monostearate, in particular polyethylene glycol 400 monostearate. Tartaric acid, citric acid and lactic acid esters of mono- and diglycerides, as well as fatty acid esters of glycerol, may also be employed as a surface active agent.

It may in certain cases be desirable to incorporate a mixture of surface active agents into the matrix, in order to improve the dispersion of the primary surface active agent in the matrix and reduce the erosion rate.

The surface active agent is typically present in any layers B) and/or C) in an amount of about 2-50%. e.g. about 5-50%, typically about 10-40%, based on the total weight of the crystalline polymer and surface active agent in the layer in question. If an active substance in layer C) possess surface active properties, a surface active agent content of less than 2% may however be employed. On the other hand, a maximum surface active agent content of about 50%, depending on the nature of the surface active agent, the active substance and the crystalline polymer, as well as on the desired delivery characteristics of the composition, will be sufficient to ensure the required repair and surfactant effects. If the content of the surface active agent exceeds about 50%, there is a risk of phase inversion, whereby the surface active agent may become the continuous phase.

As a result of the substantially constant and pH-independent erosion of the matrix of any layer C), a substantially zero order release of the active substance from the matrix of this layer will be obtained. the term "zero order" referring to the fact that the release rate of the active substance is substantially constant with time. With regard to the active substance located in layer A), the result of the constant erosion rate of the matrix of layer B) and/or C) will be a strictly controlled pulsatile release of the active ingredient in layer A). The release of the active agent from layer A) will thus essentially be based on the dissolution of the active substance in the aqueous phase at a predetermined time as a result of the erosion of layer B) and/or C).

These two release patterns (i.e. zero order and pulsatile) may also be combined, so that a uniform release of one active substance (for example at a fairly low dosage level) alternates with the release in bursts of the same or another active substance (for example at a higher dosage level).

In the layers B) or C). it may be desirable to add one or more fillers in order to modify the dispersion of the surface active agent and reduce the erosion rate of the matrix. It may similarly also be desirable to add one or more fillers to layer B) for the same purpose. It is believed that the addition of a filler serves to increase the viscosity of the mixture, whereby the surface active agent becomes more uniformly dispersed in the matrix. Examples of suitable fillers are diluents such as dicalcium phosphate, calcium sulfate, lactose or sucrose or other disaccharides, cellulose, cellulose derivatives, kaolin, mannitol, dry starch, glucose or other monosaccharides, dextrin or other polysaccharides, sorbitol, inositol or mixtures thereof; binders such as acacia, sodium alginate starch, gelatin, saccharides (including glucose, sucrose, dextrose and lactose), molasses, extract of Irish moss, panwar gum, ghatti gum, mucilage of isapol husk carboxymethylcellulose, methylcellulose, veegum, larch arabolactan, polyethylene glycols, ethylcellulose, water, alcohols, waxes, polyvinylpyrrolidone or mixtures thereof; lubricants such as talc, magnesium stearate, calcium stearate, stearic acid, hydrogenated vegetable oils, sodium benzoate, sodium chloride, leucine, carbowax 4000, magnesium lauryl sulfate, colloidal silicon dioxide and mixtures thereof; disintegrants such as starches, clays, cellulose derivatives including croscarmellose, gums, algins, various combinations of hydrogencarbonates with weak acids (e.g. sodium hydrogencarbonate/tartaric acid or citric acid) crospovidone, sodium starch glycolate, agar, cation exchange resins, citrus pulp, veegum HV, natural sponge, bentonite or mixtures thereof; volatile solvents such as alcohols, including aqueous alcohols, petroleum benzine, acetone, ether or mixtures thereof; plasticizers such as sorbitol and glycerine; and others such as dextrin, sucralfate, calcium hydroxyl-apatite, calcium phosphate and fatty acid salts such as magnesium stearate. The filler may be added in an amount so that the combination of the filler and the active substance comprises up to about 60%, typically up to about 50%, by weight of the layer.

Shape

The geometric form of the composition is important for the obtainment of the above-mentioned controlled zero order or pulsatile release. Thus, in one preferred version of the invention, the composition of the invention has a geometric shape which enables a substantially constant surface area to become exposed during erosion of the matrix. The composition may thus have the shape of a cylindrical rod which is provided with a coating having at least one opening exposing one of the layers A), B) or C) to the aqueous phase. Preferably, the layers are arranged in a substantially transverse manner and the composition is provided with a coating and has, exclusive of the coating, substantially the shape of a cylindrical rod, the coating having an opening at one or both ends. The term "cylindrical rod", as used in the context of the present invention, is understood to comprise not only those geometrical forms having a substantially circular cross-section, but also other substantially cylindrical forms, e.g. those having a constant cross-section, for example an oval or ellipse or any polygonally shaped cross-section.

In another preferred embodiment, the composition has the shape of a tablet or a pill, in which case a matrix layer B) or C) will serve as a slowly erodible coating, the composition and thickness of the matrix layer determining the time at which the active substance in an interior layer A) of the tablet or pill is released.

The transverse layers in a composition of an invention having the shape of a cylindrical rod may of course be arranged in any suitable manner in order to provide the desired release profile of the active substance(s). When such a cylindrical rod composition is provided with a coating which is eroded in the aqueous phase at a substantially slower rate than the transverse layers of the composition, the coating will typically have an opening at both ends, while a cylindrical rod shaped composition with a non-erodible coating (i.e. a coating which is self-supporting during the intended release period or which disintegrates or crumbles after the erosion of the transverse layers) may have a coating which is open at either one or both ends. Thus, the arrangement of the transverse layers will also depend on whether the coating has an opening at one end or both ends. In the case of a composition with an opening at both ends, the layers will typically have the same arrangement from each open end, resulting in a symmetrical arrangement of the layers. On the other hand, the layers in a composition with an opening in only one end will often be arranged assymetrically.

Obviously, there are a great number of possibilities as to how the layers will be arranged in any given composition, depending on the factors described above. A number of these situations are described below with reference to FIGS. 1-6, which illustrate the arrangement of the transverse layers in various compositions of the invention having an opening in one end and both ends, respectively, and with reference to FIGS. 7-10, which illustrate some of the release profiles which may be obtained by use of various compositions of the invention.

It will also be understood by a person skilled in the art that the specific finished form of the composition of the invention may comprise certain minor modifications in order to facilitate the use of the composition in question. For example, a cylindrical rod-shaped composition for delivery of a pharmaceutical powder may have rounded ends so as to avoid possible injury or discomfort when the composition is introduced into the body.

Coating

The coating may comprise a matrix of one or more substantially water soluble crystalline polymers and a surface active agent. The coating in in this case one which is eroded in the aqueous phase at a substantially slower rate than the transverse layers of the composition, whereby a substantially constant area of layers B) and/or C) is exposed during erosion of the composition, and whereby the coating is substantially eroded upon erosion of all layers A), B) and/or C).

Alternatively, the coating may be self-supporting, i.e. a coating which is substantially insoluble in and impermeable to aqueous phases during the intended release period.

The coating may further be one which disintegrates or crumbles after erosion of layers A), B) and/or C). A coating of this type would remain intact as long as it was supported by the transverse layers, but it would lack the ability to remain intact after erosion of the matrix, whereby it would then disintegrate or crumble, so that it would not remain in e.g. a human or animal for any significant amount of time after the complete erosion of the matrix and the release of the active substance.

Polymers useful as coatings are preferably those which are suitable for processing by extrusion, solution or in the form of a dispersion. Most preferred are those which are available in a food grade or pharmaceutical grade quality.

Examples of polymers useful as erodible coating materials are polyglycols, e.g. in the form of a homopolymer and/or copolymer. Preferred polymers are polyethylene glycols and/or block copolymers of ethylene oxide and propylene oxide. Polyethylene glycols which are suitable for use in an erodible coating are those having a molecular weight of from about 10,000 to about 500,000 daltons, typically from about 15,000 to about 500,000 daltons, more typically from about 20,000 to about 400,000 daltons, and especially from about 25,000 to about 300,000 daltons. Particularly interesting polyethylene glycols are those having a MW of about 35,000, 100,000 and 200,000. Typical block copolymers may be comprised of up to about 30% by weight of the polypropylene oxide based block, and have a molecular weight of above about 5000 daltons, typically about 5000 to about 30,000 daltons, more typically about 8000 to about 15,000 daltons.

Examples of self-supporting, water insoluble coating materials are polyurethanes, including Estane F 30 ®, butadiene-styrene block copoolymers, including Karton ®, and polyesters.

Examples of coating materials which disintegrate or crumble after erosion of the transverse layers of the composition are cellulose acetate, polyamide, polyethylene, polyethylene terephtalate, polypropylene, polyurethane, including Estane F 30 ®, polyvinyl acetate, polyvinyl chloride, silicone rubber, latex, polyhydroxybutyrate, polyhydroxyvalerate, teflon, polylactic acid or polyglycolic acid and copolymers thereof, copolymers such as ethylene vinyl acetate (EVA), styrene-butadiene-styrene (SBS) and styrene-isoprene-styrene (SIS), and long chain fatty acids having 12 to 20 carbon atoms, such as lauric acid, myristic acid, palmitic acid, stearic acid and arachidic acid.

In order to influence the properties of the coating material (e.g. the erosion rate, the strength of the coating and/or the ability to disintegrate or crumble), the coating may include one or more excipients such as diluents such as dicalcium phosphate, calcium sulfate, lactose or sucrose or other disaccharides, cellulose, cellulose derivatives, kaolin, mannitol, dry starch, glucose or other monosaccharides, dextrin or other polysaccharides, sorbitol, inositol or mixtures thereof; binders such as acacia, sodium alginate, starch, gelatin, saccharides (including glucose, sucrose, dextrose and lactose), molasses, extract of irish moss, panwar gum, ghatti gum, mucilage of isapol husk, carboxymethylcellulose, methylcellulose, veegum, larch arabolactan, polyethylene glycols, ethylcellulose water, alcohols, waxes, polyvinylpyrrolidone or mixtures thereof; lubricants such as talc, magnesium stearate, calcium stearate, stearic acid, hydrogenated vegetable oils, sodium benzoate, sodium chloride, leucine, carbowax 4000, magnesium lauryl sulfate, colloidal silicon dioxide and mixtures thereof; disintegrants such as starches, clays, cellulose derivatives including croscarmellose, gums, algins, various combinations of hydrogencarbonates with weak acids (e.g. sodium hydrogencarbonate/tartaric acid or citric acid) crospovidone, sodium starch glycolate, agar, cation exchange resins, citrus pulp, veegum HV, natural sponge, bentonite or others mentioned above or mixtures thereof; volatile solvents as e.g. alcohols, aqueous alcohols, petroleum benzine, acetone, ether or mixtures thereof; plasticizers as e.g. sorbitol, glycerine, polyethylene glycols and mixtures thereof; others such as cocoa butter, polyethylene glycols with a molecular weight (MW) from about 1,000 to about 10,000, in particular with a MW about 4,000, and mixtures thereof, hydrogenated vegetable oils, glycerinated gelatin or mixtures thereof. Furthermore, excipients such as dextrin, sucralfate, calcium hydroxyl-apatite, calcium phosphate and fatty acids salts such as magnesium stearate may be included.

An erodible coating may comprise one or more active substances to be released during erosion of the coating.

The coated composition may furthermore be enteric coated in cases where the drug is sensitive to the environment in the stomach, e.g. when the drug is degraded by gastric acid, or where it is undesirable for therapeutic reasons to expose the stomach to drug, e.g. when the drug causes irritation of the gastric mucosa. Furthermore, it may be desirable to target the release to a given segment in the intestines. This can be done because the passage time through the small intestine is relatively constant (4-6 hours), while the passage time through the stomach is dependent on numerous factors and therefore is rather unpredictable. The enteric coating may include an active substance intended for immediate release in the intestines.

Materials suitable for enteric coating include cellulose acetate phthalate, formalin-treated gelatin, polyvinyl acetate phthalate, hydroxypropyl methylcellulose phthalate, methacrylic acid- methacrylic acid ester co-polymers and mixtures thereof.

Coatings to improve the appearance and or taste, e.g. film or sugar coating, may be applied to the composition. Release of an active substance before the onset of release by the composition of the invention (initial burst release) may be effectuated by incorporating the active substance in the external coating.

A method of preparing a composition according to the invention which has the shape of a cylindrical rod comprising substantially transverse layers and which is provided with a coating is to first prepare a core of layers comprising at least one layer A) of the active substance and at least one layer B) and/or C) of a matrix of a crystalline polymer and a surface active agent, followed by the formation of the coating around the obtained core. This will typically be accomplished by using injection molding or extruding.

An example of a method for preparing the composition by use of injection molding is described below with reference to FIG. 11. In this method, the transverse layers are first formed by injection, starting with the layer(s) in the center of the composition, after which the coating is injected around the core of transverse layers.

Alternatively, a composition in the shape of a cylindrical rod comprising substantially transverse layers and a coating may be prepared by first preparing the individual transverse layers, e.g. using conventional techniques for the preparation of pharmaceutical tablets. The individual matrix layers may for example be prepared by first pre-mixing all the ingredients (in powder form), with the exception of the surface active agent, to be included in the particular layer, in a high shear mixer. The ingredients are mixed in the mixer to produce a homogeneous pre-mix to which the melted surface active agent is added while mixing. This mixture is then compounded, for example in a double screw extruder, and extruded through a multiplicity of holes or nozzles to produce pellets which typically have a diameter of about 2-3 mm and a length of about 3-4 mm. These pellets are then used to produce the individual matrix layers using conventional extrusion or injection techniques known in the field of polymer technology.

The individual layers are then joined together, for example by using a low-melting polyethylene glycol e.g. polyethylene glycol 1500, as a hot-melt adhesive, or by compressing the individual layers and using ultrasonic welding.

A composition having the shape of a tablet or a pill comprising an external matrix layer B) or C) and an interior layer A) may be prepared using conventional techniques known in the pharmaceutical industry, taking into consideration the composition of the particular matrix layer used so as to ensure the release of the active substance in the interior layer A) at the desired time after administration.

Coating of a composition may be performed using conventional techniques known in the pharmaceutical industry e.g. dip coating or solvent coating by dipping or spraying. Furthermore, a coated composition can be obtained by injection molding, compression molding or extrusion of the transverse layers into a pre-formed coating.

BRIEF DESCRIPTION OF THE DRAWINGS

The invention is further described in the following with reference to the accompanying drawings.

FIG. 11a-e shows a method for producing a composition according to the invention.

FIG. 1 shows a composition which provides a timed burst release of an active substance, optionally combined with an initial continuous release of the same or another active substance. The composition consists of a layer 2 of a crystalline polymer matrix and a surface active agent, a layer 3 of an active substance, and a coating 1 which is insoluble or which disintegrates or crumbles after erosion of layers 2 and 3. The matrix layer 2 may be without an active substance, in which case a release profile equivalent to that shown in FIG. 7 may be obtained. Alternatively, the matrix layer 2 may comprise an active substance substantially homogeneously dispersed therein. When the active substance in layer 2 is the same as that of layer 3, a release profile equivalent to that shown in FIG. 8 may be obtained, and when the active substance in layer 2 is different from that of layer 3, a release profile equivalent to that shown in FIG. 10 may be obtained.

FIG. 2 shows a composition which provides a timed burst release of an active substance and which has an erodible coating. The composition consists of a two layers 2 of a crystalline polymer matrix and a surface active agent, a layer 3 of an active substance, and a coating 1 which comprises a crystalline polymer matrix and a surface active agent, the coating being one which is eroded by an aqueous phase at a substantially slower rate than matrix layers 2, whereby a substantially constant area of layers 2 is exposed during erosion of the composition, and whereby the coating is substantially eroded upon erosion of layers 2 and 3. The matrix layers 2 may be without an active substance, in which case a release profile equivalent to that shown in FIG. 7 may be obtained. Alternatively, the matrix layers 2 may comprise an active substance substantially homogeneously dispersed therein. When the active substance in layers 2 is the same as that of layer 3, a release profile equivalent to that shown in FIG. 8 may be obtained, and when the active substance in layers 2 is different from that of layer 3, a release profile equivalent to that shown in FIG. 10 may be obtained.

FIG. 3 shows a composition which provides an initial burst release and a timed burst release of an active substance, optionally combined with a continuous release of the same or another active substance between the bursts. The composition consists of a layer 2 of an active substance, a layer 3 of a crystalline polymer matrix and a surface active agent, a second layer 4 of the active substance, and a coating 1 which is insoluble or which disintegrates or crumbles after erosion of layers 2, 3 and 4. The matrix layer 3 may contain an active substance substantially homogeneously dispersed therein, which may be the same as or different from the active substance of layers 2 and 4. Alternatively the matrix layer 3 may be without an active substance. When the matrix layer 3 comprises an active substance which is the same as that of layers 2 and 4, a release profile equivalent to that shown in FIG. 9 may be obtained.

FIG. 4 shows a composition which provides an initial burst release and a timed burst release of an active substance optionally combined with a continuous release of the same or another active substance between the bursts, the composition having an erodible coating. The composition consists of two layers 2 of an active substance, two layers 3 of a crystalline polymer matrix and a surface active agent, a third layer 4 of the active substance and a coating 1 which comprises a crystalline polymer matrix and a surface active agent, the coating being one which is eroded by an aqueous phase at a substantially slower rate than matrix layers 3, whereby a substantially constant area of layers 3 is exposed during erosion of the composition, and whereby the coating is substantially eroded upon erosion of layers 2, 3 and 4. The matrix layers 3 may contain an active substance substantially homogeneously dispersed therein, which may be the same as or different from the active substance of layers 2 and 4. Alternatively the matrix layers 3 may be without an active substance. When the matrix layers 3 comprises an active substance which is the same as that of layers 2 and 4 a release profile equivalent to that shown in FIG. 9 may be obtained.

FIG. 5 shows a composition which provides timed double burst releases of one or two active substances. The composition comprises a layer 2 of a crystalline polymer matrix and a surface active agent, a layer 3 of an active substance a second layer 4 of a crystalline polymer matrix and a surface active agent, a second layer 5 of an active substance, and a coating 1 which is insoluble or which disintegrates or crumbles after erosion of layers 2, 3, 4 and 5. The active substance in layers 3 and 5 may be the same or different. The matrix layers 2 and 4 may be without an active substance, in which case they will function as a timer for release of the active substance(s) in layers 3 and 5. Alternatively the matrix layers 2 and 4 may contain an active substance substantially homogeneously dispersed therein.

FIG. 6 shows a composition which provides timed double burst releases of one or two active substances, and which has an erodible coating. The composition comprises two layers 2 of a crystalline polymer matrix and a surface active agent, two layers 3 of an active substance, two second layers 4 of a crystalline polymer matrix and a surface active agent, a second layer 5 of an active substance, and a coating 1 which comprises a crystalline polymer matrix and a surface active agent, the coating being one which is eroded by an aqueous phase at a substantially slower rate than matrix layers 2 and 4, whereby a substantially constant area of layers 2 and 4 is exposed during erosion of the composition, and whereby the coating is substantially eroded upon erosion of layers 2, 3, 4 and 5. The active substance in layers 3 and 5 may be the same or different. The matrix layers 2 and 4 may be without an active substance, in which case they will function as a timer for release of the active substance(s) in layers 3 and 5. Alternatively the matrix layers 2 and 4 may contain an active substance substantially homogeneously dispersed therein.

FIG. 7 shows a release profile for a composition which provides a single timed burst release of an active substance, for example for the treatment of rheumatoid arthritis. The composition is timed so that the active substance is released at a predetermined period of time after administration, typically a number of hours, thereby providing a dosis of the active substance above the analgetic level. A composition providing such a release profile may thus, for example, be administered in the evening, thereby providing an analgetic dose of an active substance in the early morning for the prevention of arthritis pain upon awakening.

FIG. 8 shows a release profile for a composition which provides a continuous release of an active substance followed by a timed burst release of the active substance. The release profile is thus similar to that shown in FIG. 7, but with the additional benefit of a low-level sustained release (above the antiinflammatory level) of the same active substance as that which is supplied in a burst at the predetermined time.

FIG. 9 shows a release profile for a composition which provides an initial burst release of an active substance, a continuous release of the active substance and finally a timed burst release of the active substance. The release profile is thus similar to that shown in FIG. 8, with the exception that an initial burst of the active substance (a dose above the analgetic level) is provided immediately after administration, this initial burst being followed by a low-level sustained release and a subsequent second burst at a higher level.

FIG. 10 shows a release profile for a composition which provides a continuous release of an active substance followed by a timed burst release of another active substance. The release profile in this case is similar to that shown in FIG. 8 with the exception that the active substance which is continuously released at a low level is different from that which is released as a timed burst.

Figure 1:
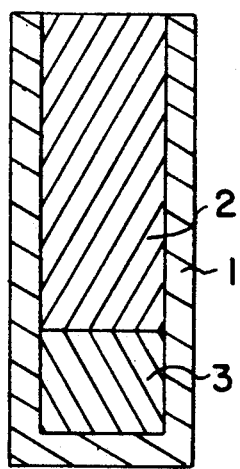
FIG. 1 shows a cross sectional view of a composition according to the invention which provides a timed burst release of an active substance.
Figure 2:
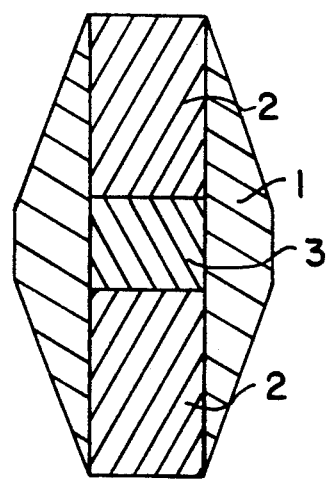
FIG. 2 shows a cross sectional view of a composition according to the invention which provides a timed burst release of an active substance and which has an erodible coating.
Figure 3:
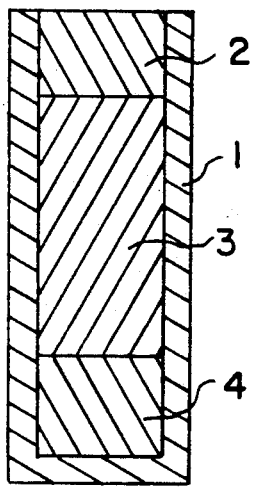
FIG. 3 shows a cross sectional view of a composition according to the invention which provides an initial burst release and a timed burst release of an active substance.
Figure 4:
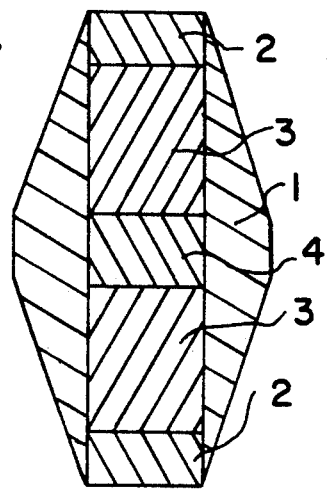
FIG. 4 shows a cross sectional view of a composition according to the invention which provides an initial burst release and a timed burst release of an active substance, and which has an erodible coating.
Figure 5:
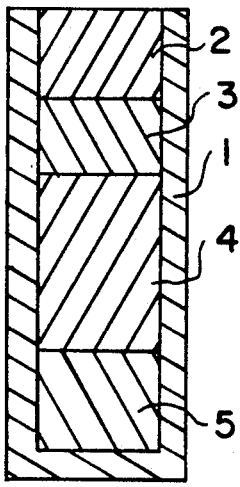
FIG. 5 shows a cross sectional view of a composition according to the invention which provides timed burst releases of one or two active substances.
Figure 6:
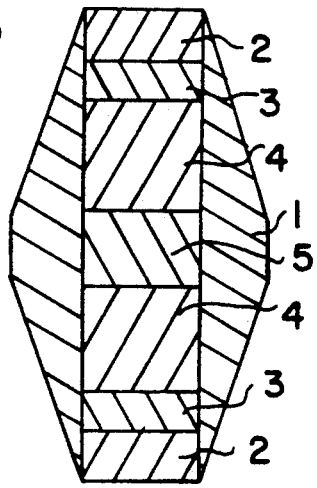
FIG. 6 shows a cross sectional view of a composition according to the invention which provides timed burst releases of one or two active substances, and which has an erodible coating.
Figure 7:
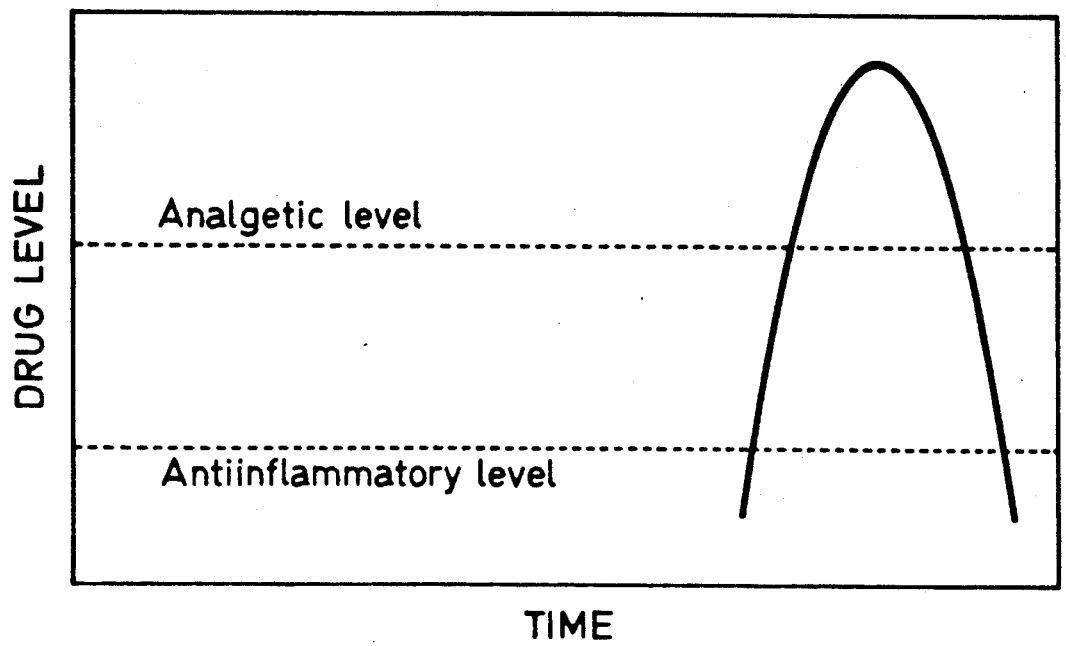
FIG. 7 shows a release profile for a composition according to the invention which provides a single timed burst release of an active substance.
Figure 8:
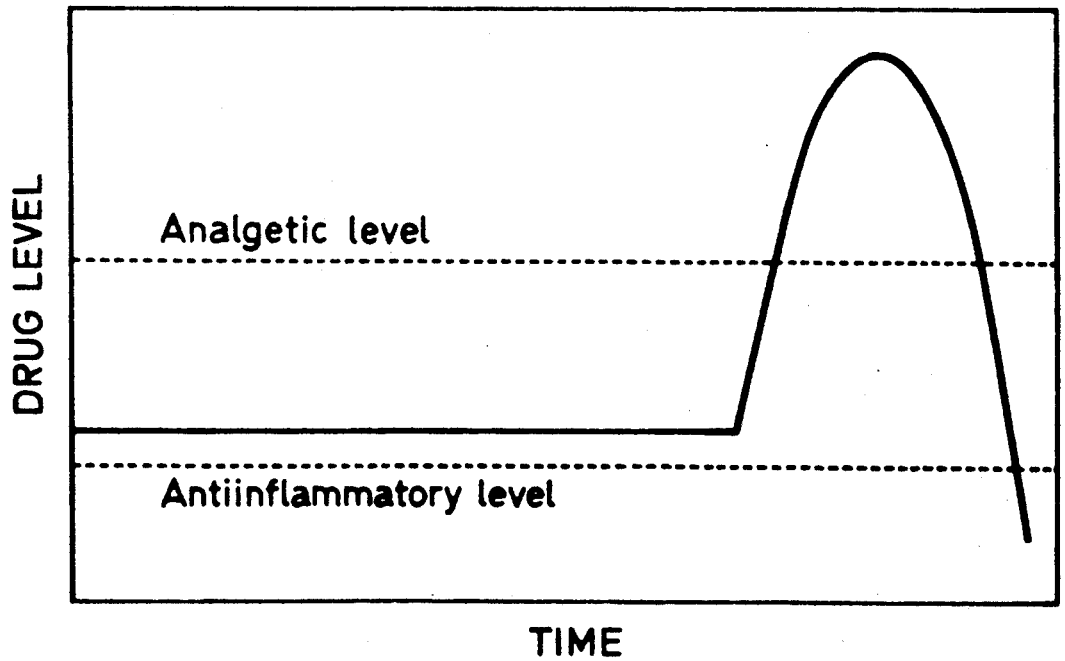
FIG. 8 shows a release profile for a composition according to the invention which provides a continuous release of an active substance followed by a timed burst release of the active substance.
Figure 9:
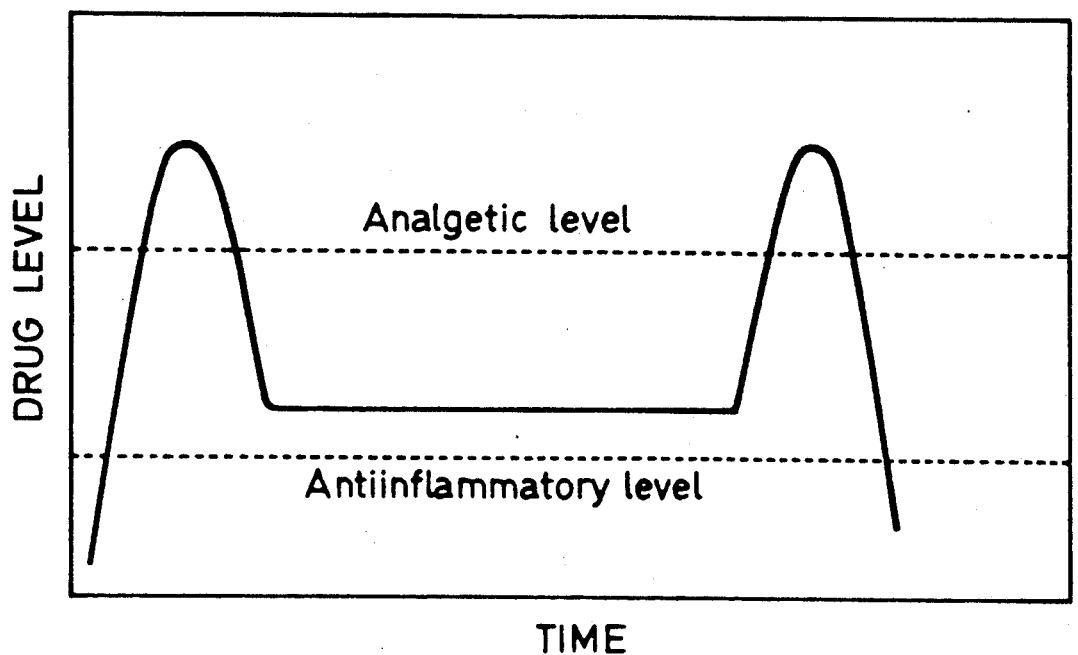
FIG. 9 shows a release profile for a composition according to the invention which provides an initial burst release of an active substance, a continuous release of the active substance and finally a timed burst release of the active substance.
Figure 10:
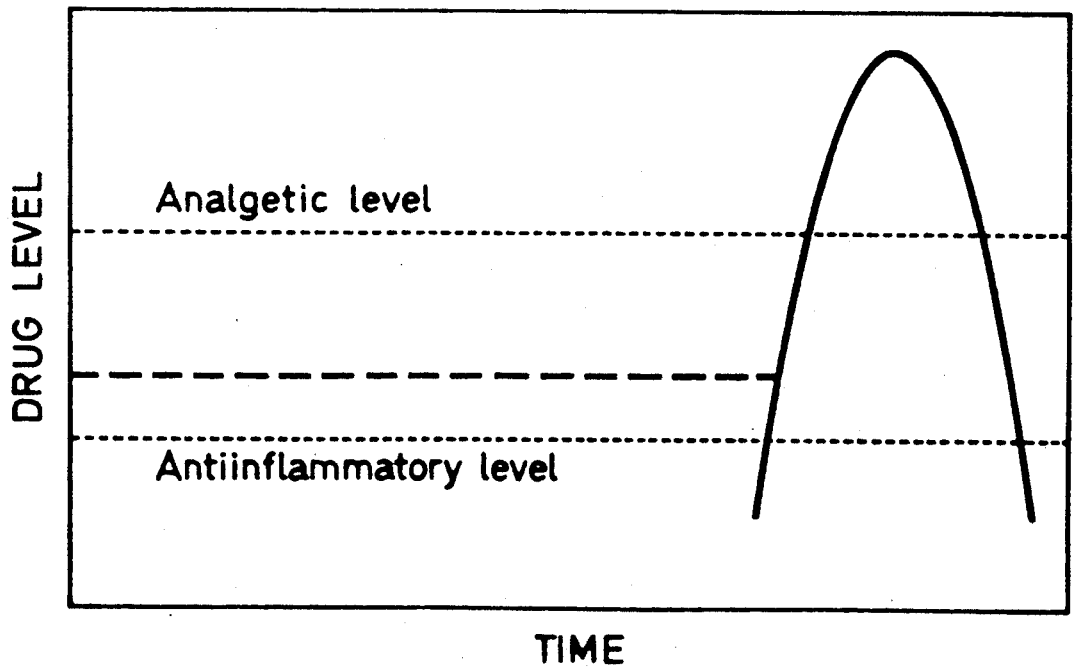
FIG. 10 shows a release profile for a composition according to the invention which provides a continuous release of an active substance followed by a timed burst release of another active substance.
Figure 11:
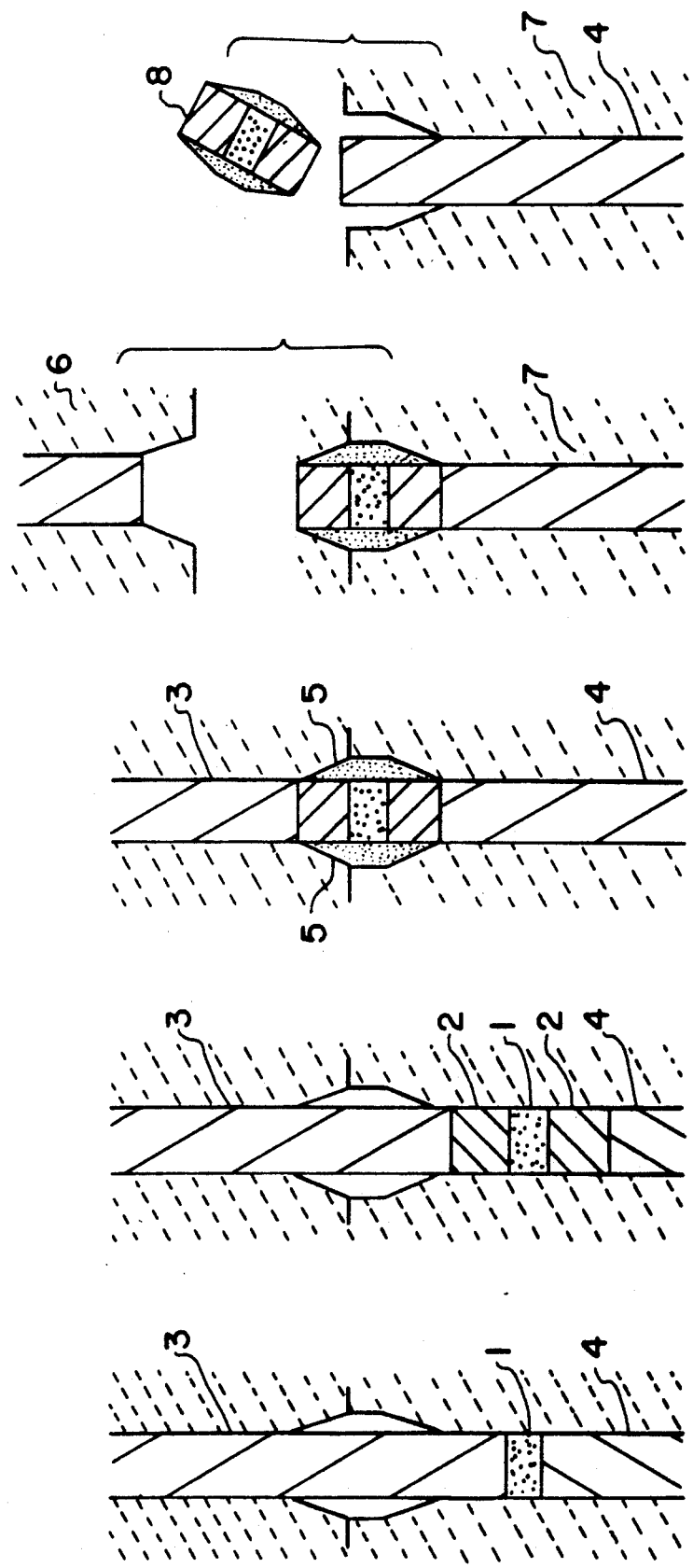
FIG. 11 shows a method for producing a composition according to the invention, the composition being one which is equivalent to that shown in FIG. 2. The figure shows a schematic cross sectional view of a series of five steps by which the composition may be produced in a mold. It is to be noted that while the figure only shows the preparation of a single unit of the composition, the preparation of the composition will in practice take place in a mold in which a multiplicity of units may be prepared simultaneously in a coordinated manner.

In step a) a layer comprising an active substance 1 dispersed in, e.g., a molten polyethylene glycol with a molecular weight of about 1.000–10.000, is injected into a central cavity formed by two pistons 3 and 4, after which the molten polyethylene glycol is allowed to solidify. In step b) the two pistons 3 and 4 have moved an equal distance away from the active substance 1 in the central cavity. Two layers 2, each of which comprises a crystalline polymer matrix and a surface active agent, are then injected into the two new cavities which are formed on either side of the active substance 1 by the movement of the two pistons 3 and 4. In step c) the two layers 2 have solidified and the two pistons 3 and 4 have moved forward, thereby pushing a central composite rod comprising the two matrix layers 2 and the active substance 1 into a new cavity into which a coating 5 is injected. In step d) the mold is opened by moving one part 6 of the mold from the other part 7. In step e) the finished composition 8 is ejected from the mold 7 by the movement of piston 4.

It will be understood by a person skilled in the art that this basic process may be altered in a variety of ways in order to prepare a composition which differs from that whose preparation is described in this figure. For example, for the preparation of a composition which has a non-erodible coating with a substantially uniform thickness, the shape of the cavity into which the coating 5 is injected may be varied. Similarly, for the preparation of a composition with a coating which is open in one end only, piston 4 may be drawn slightly back prior to the injection of the coating 5, whereby a coating which covers one end of the composition will be formed. The number and arrangement of the individual transverse layers may furthermore be varied, for example to prepare compositions having different release profiles.

Figure 12:
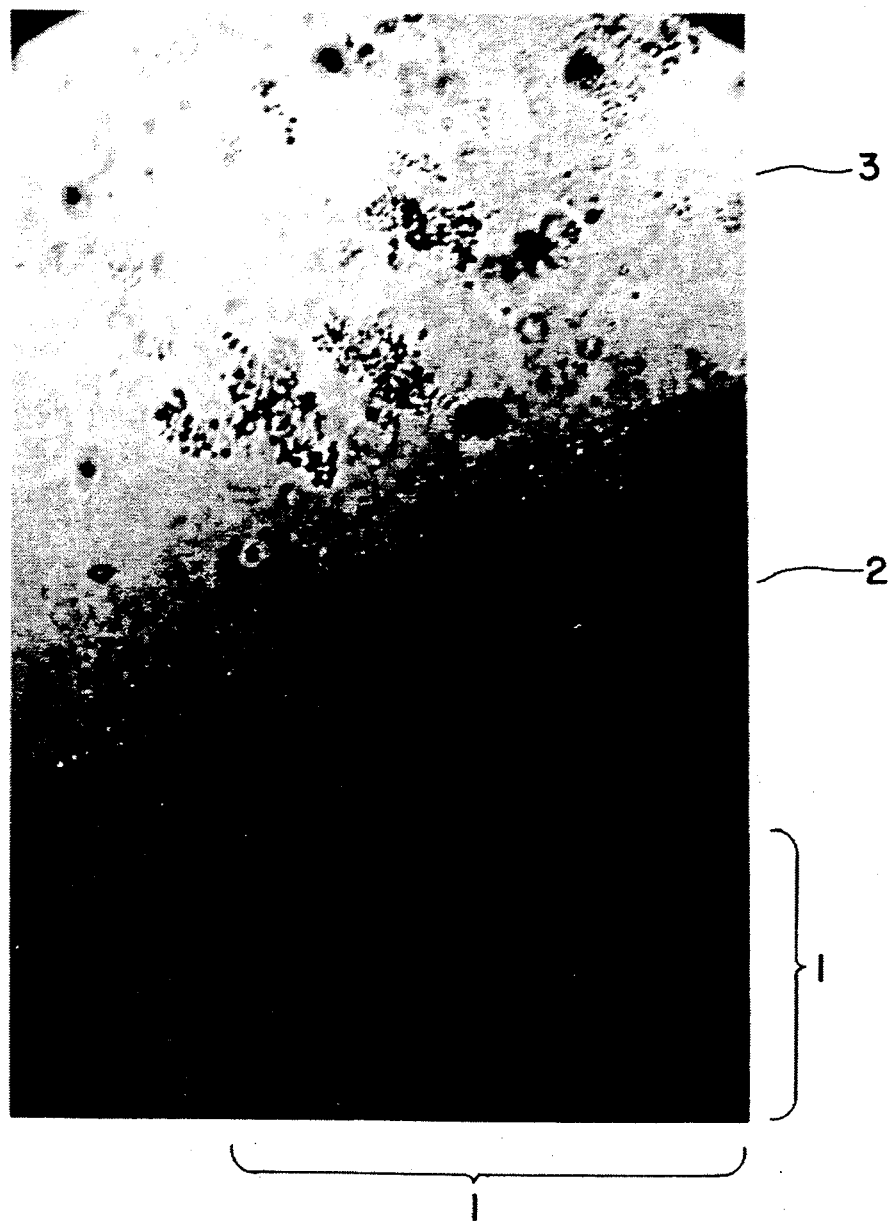
FIG. 12 shows a copy of a photograph of the erosion of a matrix layer C) of a composition of the invention in an aqueous medium.

FIG. 12 shows a copy of a photograph of the erosion of a matrix layer C) of a composition of the invention in an aqueous medium (Revolyt). Three distinct zones may be seen. Zone 1 is a matrix of crystalline polyethylene 35,000 in which polyethylene glycol 400 monostearate and an active substance is dispersed. Zone 2 is a wet "erosion zone" containing globules of polyethylene glycol 400 monostearate and the active substance in polyethylene glycol 35,000 dissolved in the aqueous Revolyt solution. Zone 3 is an aqueous zone with a few grains of the active substance, which is believed to be surrounded by polyethylene glycol 400 monostearate. It may be observed that the original border between the matrix and the aqueous solution, i.e. between zones 2 and 3, is approximately parallel with the present erosion border, i.e. the border between zones 1 and 2, indicating that the matrix has eroded at a substantially constant rate as measured from the original surface prior to the start of erosion by the aqueous medium.

EXAMPLE 1

General Method

The PEG in question was heated to 50°–80° C. until molten. If present, excipients and/or active substances were mixed therein. The molten matrix was extruded into a pre-formed teflon tube with an internal diameter of 6 mm and left to cool. The cooled matrix was then pushed from the tube by means of a piston, and the resulting rod was coated with a 20% solution of polyurethan (Estane 5712 F 30) in acetone. The coated rod was subsequently cut into segments with a length of 20 mm.

The erosion rate in 100 ml simulated intestinal juice (Revolyt; composition: 22 mmol/l of hydrogen carbonate 15 mmol/l of potassium 60 mmol/l of chloride 3 mmol/l of magnesium, 67 mmol/l of sodium and 3 mmol/l of sulphate) with constant shaking on an orbital shaker (Koterman 4019) (60 rpm) at 37° C. was measured over a period of 6 hours. The diameter of rotation of the shaker was 27.5 mm. The composition was centrally placed in a 100 ml bottle). If the weight of the composition was less than 0.40 g, an additional weight was added until to a total weight of about 0.40–0.43 g was achieved.

Compositions of 100% PEG having a molecular weight (MW) of 10,000, 35,000, 100,000 and 200,000, of 95% PEG 35,000 and 5% PEG 400 monostearate and of 35% PEG 35,000, 40% dextrin and 25% PEG 400 monostearate, respectively, were prepared according to the above general method. The erosion rates were measured and the results are shown below:

| Ingredients | Erosion rate (mm/h) |
| --- | --- |
| 100% PEG 10,000 | 4 |
| 100% PEG 35,000 | 1.8 |
| 100% PEG 100,000 | 1.2 |
| 100% PEG 200,000 | 0.56 |
| 95% PEG 35,000 and 5% PEG 400 monostearate | 1.45 |
| 35% PEG 35,000, 40% dextrin and 25% PEG 400 monostearate | 0.34 |

The results show that the erosion rate decreases as the molecular weight of the PEG increases. Furthermore, addition of PEG 400 monostearate or a filler such as dextrin lower the erosion rate.

EXAMPLE 2

The following compositions were prepared and the erosion rates determined according to the methods described in Example 1.

TABLE 1

| Ingredients | A[a] | B[a] | C[a] |
|---|---|---|---|
| PEG 10,000 | | | |
| PEG 20,000 | | | |
| PEG 35,000 | 55 | 45 | 35 |
| PEG 400 monostearate | 5 | 15 | 25 |
| Dextrin | 39 | 39 | 39 |
| Tartrazin | 1 | 1 | 1 |
| Erosion rate (mm/h) | 0.65 ± 0.2[b] | 0.50 ± 0.2 | 0.50 ± 0.2 |
| Ingredients | D[a] | E[a] | F[a] |
| PEG 10,000 | 45 | | |
| PEG 20,000 | | 45 | |
| PEG 35,000 | | | 55 |
| PEG 400 monostearate | 15 | 15 | 5 |
| Dextrin | 39 | 39 | 39 |
| Tartrazin | 1 | 1 | 1 |
| Erosion rate (mm/h) | 0.5 ± 0.3[c] | 0.60 ± 0.3[c] | 0.73 ± 0.2[d] |

[a] the values given are in % by weight
[b] standard deviation
[c] the erosion is uneven (i.e. the surface area is not constant)
[d] the erosion is very uneven the results indicate that addition of various amounts of PEG 400 monostearate has no significant influence on the erosion rate of PEG 35,000 matrices comprising a relatively large amount of a filler. The PEG 10,000 and PEG 20,000 matrices erode unevenly, and the unevenness is greatest when the matrix contains 5% PEG 400 monostearate. An uneven erosion is a disadvantage as the surface area exposed to the aqueous medium will not be constant.

EXAMPLE 3

The following compositions were prepared and the erosion rates determined according to the methods described in Example 1.

TABLE 2

| Ingredients | A[b] | B[b] |
|---|---|---|
| PEG 35,000 | 20 | 40 |
| PEG 400 monostearate | 10 | 20 |
| DAT S[a] | 20 | |
| Sucralfate | 50 | 40 |
| Erosion rate (mm/h) | 0.12 | 0.25 |

[a] Surfactant, Grindsted Products, Denmark, diacetylated tartaric acid ester of mono-diglycerides prepared from refined fat
[b] the values given are in % by weight The results show that slowly erodible matrices can be obtained by addition of sucralfate and/or a surfactant. Such a matrix composition may be suitable for use as an erodible coating material.

EXAMPLE 4

Matrix layers were prepared by first melting 5.4 g of polyethylene glycol 35,000 and 1.8 g of polyethylene glycol 400 monostearate in an oven at 90° C. 4.37 g of dextrin and 0.426 g of morphine hydrochloride were then added, after which the molten mass was stirred vigorously. The molten mass was then extruded into a teflon tube (diameter 6 mm) and cooled. After cooling, matrix layers were prepared by cutting the obtained rod into segments having the desired length of 3.52 mm. Each matrix layer contained 4.02 mg of morphine chloride.

Burst layers were prepared by first melting 9 g of polyethylene glycol 1500 after which 2.45 g of microcrystalline cellulose (Avicel) and 2.16 g of morphine hydrochloride were added. This mixture was stirred vigorously, and the mass was extruded into a 6 mm diameter teflon tube prior to cooling. After cooling, burst layers with a diameter of 6 mm were prepared by cutting the obtained rod into the desired length of 1.93 mm. Each burst layer contained 9.9 mg of morphine chloride.

A "sandwich" composition was prepared with the above-obtained layers by "glueing" a matrix layer onto each end of a burst layer using molten polyethylene glycol 1000. An auxiliary rod of polyethylene glycol 1500 (length 20 mm, diameter 6 mm) was then glued onto each end of the sandwich composition.

The composition was coated 3 times with polyurethane (20% Estane F30) in tetrahydrofuran. After drying of the coating, the auxiliary rods were removed from the composition by cutting them off, followed by removal by melting of any excess polyethylene glycol 1500.

The release of morphine HCl from the compositions was tested in vitro in Revolyt at 37° C. with agitation, measuring by HPLC.

Eluent: 80/10/15 (parts by volume) 1% ammonium acetate/acetonitrile/dioxan.

Loop: 20 μl, C18 column 12.5 mm. flow: 1 ml/min. 80 −254 mm

The following results were obtained:

TABLE 3

| Time (hours) | (mg/h) | (mg/h) | (mg/h) |
|---|---|---|---|
| 1 | 0.94 | 1.23 | 1.25 |
| 2 | 0.82 | 1.02 | 1.97 |
| 3 | 0.78 | 0.96 | 0.91 |
| 4 | 0.73 | 0.75 | 0.81 |
| 5 | 0.75 | 0.94 | 0.83 |
| 6 | 0.72 | 1.01 | 0.76 |
| 7 | 0.74 | 1.87 | 3.24 |
| 8 | 0.42 | 7.2 | 5.54 |
| 9, end | 13.59 | 4.24 | 4.44 |
| Total | 19.49 | 19.22 | 19.75 |

EXAMPLE 5

Matrix layers were prepared by first melting 5.4 g of polyethylene glycol 35,000 and 1.8 g of polyethylene glycol 400 monostearate in an oven at 90° C. 4.79 g of dextrin was then added, after which the molten mass was stirred vigorously. The molten mass was then extruded into a teflon tube (diameter 6 mm) and cooled. After cooling, matrix layers were prepared by cutting the obtained rod into segments having the desired length of 3.0 mm.

Burst layers were prepared by first melting 3.5 g of polyethylene glycol 1500, after which 1.5 g of morphine hydrochloride were added. This mixture was stirred vigorously, and the mass was extruded into a 6 mm diameter teflon tube prior to cooling. After cooling, burst layers with a diameter of 6 mm were prepared by cutting the obtained rod into the desired length of 1.0 mm. Each burst layer contained 10.5 mg of morphine chloride.

A "sandwich" composition was prepared with the above-obtained layers by "glueing" a matrix layer onto each end of a burst layer using molten polyethylene glycol 1000. An auxiliary rod of polyethylene glycol 1500 (length 20 mm, diameter 6 mm) was then glued onto each end of the sandwich composition.

The composition was coated 3 times with 20% Estane F30 in tetrahydrofuran. After drying of the coating, the auxiliary rods were removed as described above in Example 4.

The release of morphine HCl from the compositions was tested in vitro in Revolyt at 37° C. with agitation, measuring by HPLC.

Eluent: 80/10/15 (parts by volume) 1% ammonium acetate/acetonitrile/dioxan.

Loop: 20 μl, C18 column 12.5 mm. flow: 1 ml/min. λ=254 mm

The following results were obtained:

TABLE 4

| Time (hours) | Egalette 1 (mg) | Egalette 2 (mg) | Egalette 3 (mg) |
| --- | --- | --- | --- |
| 1 h | 0 | 0 | 0 |
| 2 h | 0 | 0 | 0 |
| 3 h | 0 | 0 | 0 |
| 4 h | 0 | 0 | 0 |
| 5 h | 0 | 0 | 0 |
| 6 h | 0 | 4.4 | 0 |
| 7 h | 7.9 | 3.1 | 4.2 |
| 8 h | 2.55 | 3.0 | 6.3 |

The compositions were further tested in vivo, measuring the serum concentration of morphine HCl using a radioimmuno assay method. The method is a competition assay based on competition between $^{125}I$ labeled morphine and unlabelled morphine for binding to a morphine antibody. The morphine antibody is produced in goats. A standard is made by assaying serum to which morphine is added to a concentration of about 2-78 ng/ml. Thus, the morphine concentration in a serum sample can be determined by reference to the standards.

The following in vivo results were obtained:

TABLE 5

| Time (hours) | Person 1[a] (ng/ml) | Person 2[a] (ng/ml) | Person 3[a] (ng/ml) |
| --- | --- | --- | --- |
| 2 | <2 | 1.3 | <2 |
| 3 | <2 | 3.4 | <2 |
| 3½ | <2 | 4.0 | <2 |
| 4 | <2 | 5.6 | <2 |
| 4½ | 7.8 | — | <2 |
| 5 | 49 | 61 | <2 |
| 5½ | >65 | >65 | <2 |
| 6 | >65 | >65 | <2 |
| 6½ | >65 | >65 | <2 |
| 7 | >65 | >65 | <2 |
| 7½ | >65 | >65 | >65 |
| 8 | >65 | >65 | >65 |

[a] The values given are the morphine serum concentration

EXAMPLE 6

Three different types of matrix layers were prepared consisting of, respectively, 1) polyethylene glycol 10,000; 2) polyethylene glycol 35,000; and 3) 45% polyethylene glycol 35,000, 15% polyethylene glycol 400 monostearate and 40% dextrin. Matrices 1) and 2) were prepared by melting the respective polyethylene glycols at 90° C. and extruding the molten masses into 6 mm diameter teflon tubes.

After cooling, layers were prepared by cutting the obtained rods into segments having a length of 8 mm for matrix 1) and 7.5 mm for matrix 2).

Matrix 3) was prepared by first melting 4.5 g of polyethylene glycol 35,000 and 1.5 g of polyethylene glycol 400 monostearate and adding 4.0 g of dextrin, after which the molten mass was stirred vigorously. The molten mass was then extruded into a teflon tube (diameter 6 mm) and cooled. After cooling, matrix layers were prepared by cutting the obtained rod into segments having the desired length of 3.75 mm.

Burst layers were prepared by first melting 4.5 g of polyethylene glycol 1500, after which 0.5 g of tartrazine were added. This mixture was into a 6 mm diameter teflon tube prior to cooling. After cooling, burst layers with a diameter of 6 mm were prepared by cutting the obtained rod into the desired length of 2.0 mm.

A "sandwich" composition was prepared with the above-obtained layers by "glueing" a matrix layer onto each end of a burst layer using molten polyethylene glycol 1000. An auxiliary rod of polyethylene glycol 1500 was then glued onto each end of the sandwich composition.

The compositions were then coated 3 times with polyurethane (20% Estane F30) in acetone. After drying of the coating, the auxiliary rods were removed as described above.

The erosion of the matrix layers of the compositions were tested in vitro in Revolyt at 37° C. with agitation (see Example 1).

Matrix 1) was eroded at a rate of 4 mm/hour, releasing tartrazine after 2 hours.

Matrix 2) was eroded at a rate of 1.9 mm/hour, releasing tartrazine after 4 hours.

Matrix 3) was eroded at a rate of 0.34 mm/hour, releasing tartrazine after 11 hours.

EXAMPLE 7

Second burst layers were prepared by first melting 0.6 g of polyethylene glycol 1500 at 90° C., after which 0.065 g of Avicel and 1 g of coffein were added. This mixture was stirred vigorously, and the mass was extruded into a 5 mm diameter teflon tube prior to cooling. After cooling, burst layers with a diameter of 5 mm were prepared by cutting the obtained rod into segments with a length of 3.5 mm. Each 3.5 mm burst layer contained 75 mg of coffein.

First burst layers were prepared as described for the second burst layers, with the exception that the molten mass was extruded into teflon tubes with a diameter of 6 mm, the rods being cut to 2.5 mm.

Matrix layers were prepared by first melting 6.96 g of polyethylene glycol 35,000 and 1.44 g of polyethylene glycol 400 monostearate at 90° C. 3.6 g of dextrin was then added, after which the molten mass was stirred vigorously. The molten mass was then extruded into a teflon tube (diameter 6 mm) and cooled. After cooling, matrix layers were prepared by cutting the obtained rod into segments having the desired length of 3.5 mm.

A "sandwich" composition was prepared with the above-obtained layers by "glueing" a second burst layer onto one end of a matrix layer and an auxiliary rod onto the other end using molten polyethylene glycol 1000.

The composition was coated 3 times with 20% Estane F30 in tetrahydrofuran. After drying of the coating, the auxiliary rods were removed about 0.5 mm over the matrix layer. The composition was placed in a 40° C. oven for 5 minutes, after which a first burst layer was glued onto the end of the matrix layer opposite the second burst layer. The finished composition was open in one end and consisted of a 50 mg first burst layer, a 3.5 mm matrix layer and a 75 mg second burst layer.

The erosion rate of the matrix layer was tested in vitro in Revolyt at 37° C. with agitation. An erosion rate of 0.55 mm/hour was found, which is equivalent to a period of about 6½ hours until the second burst is released.

The compositions were further tested in the following dissolution test.

Reagents and Apparatus

Dissolution system: Sotax AT6 dissolution apparatus in accordance with USP XXI <711> apparatus 2 (paddle stirring element), automatic working apparatus with filters at the top connected to an ISCO dissolution sampler with plastic tubes. The fluid is gathered in the sampler by a 6 channel peristaltic pump.

Paddle speed: 100 rotations per minute.
Dissolution medium: 900 ml pH 6.8 phosphate buffer.
Spectrophotometer: Lamda 5, Perkin-Elmer or equivalent apparatus.
Standard solution: 5–10 μg/ml of coffeine in the dissolution medium.

Procedure

The test was carried out according to USP XXI <711>. 9 ml samples were withdrawn at ¼, ½, 1, 3, 6, 6½, 7, 7½, 8 and 8½ hours. The withdrawn media was not replaced.

Analytical Method

The withdrawn samples were diluted to one tenth of the original strength with dissolution medium and the absorbances of the dilutions were measured at $\lambda=272$ nm against a blank. The absorbance of the standard solution against a blank was also measured and from those values, the amount of coffein released could be calculated, taking into consideration the degree of dilution and the volume of the dissolution medium.

TABLE 6

Dissolution by USP-paddle, 100 rpm, pH 6.8, n = 6 in % of declared amount

| Sample | ¼ h | ½ h | 1 h | 3 h |
|---|---|---|---|---|
| 1 | 33.02 | 47.87 | 50.81 | 51.26 |
| 2 | 48.25 | 49.63 | 49.17 | 50.29 |
| 3 | 47.10 | 47.79 | 47.56 | 47.78 |
| 4 | 51.26 | 50.57 | 50.12 | 50.57 |
| 5 | 35.79 | 52.47 | 52.70 | 52.47 |
| 6 | 51.02 | 53.77 | 53.54 | 53.54 |
| x | 44.4 | 50.7 | 51.0 | 52.7 |
| $s_{abs}$ | 8.0 | 2.4 | 2.2 | 2.0 |

| Sample | 5 h | 6 h | 6½ h | 7 h |
|---|---|---|---|---|
| 1 | 50.60 | 51.04 | 51.04 | 51.24 |
| 2 | 51.62 | 68.73 | 80.67 | 89.90 |
| 3 | 57.31 | 77.93 | 88.13 | 96.72 |
| 4 | 50.34 | 51.22 | 57.30 | 65.89 |
| 5 | 52.03 | 59.27 | 69.89 | 81.07 |
| 6 | 53.98 | 59.98 | 66.19 | 74.13 |
| x | 52.7 | 61.2 | 68.9 | 76.5 |
| $s_{abs}$ | 2.6 | 10.5 | 13.9 | 16.5 |

| Sample | 7½ h | 8 h | 8½ h |
|---|---|---|---|
| 1 | 58.17 | 65.40 | 75.79 |
| 2 | 101.33 | 109.87 | 116.60 |
| 3 | 107.76 | 110.84 | 112.57 |
| 4 | 79.63 | 90.59 | 99.04 |
| 5 | 96.34 | 106.86 | 99.49 |
| x | 88.0 | 96.0 | 103.1 |
| $s_{abs}$ | 17.9 | 17.4 | 15.5 |

From the table, it is seen that initially about 40–50% of the declared amount is released, corresponding to the initial dose of 50 mg of coffein (app. 40% of the declared amount). After a period of about 6–6½ hours the second burst dose is released and the total dose is released after about 8–8½ hours.

EXAMPLE 8

An insulin composition (A) was prepared by mixing and melting 6.96% human insulin*, 80.68% PEG 2000 6.87% Avicel 5.49% amylopectin-SO₄.

Another insulin composition (B) was prepared by mixing 7.37% human insulin*, 85.37% PEG 2000, 7.26% Avicel.

(* Human Insulin Novo Nordisk, Batch No. 111223)

The molten mass was stirred vigourously and then extruded into a teflon tube (diameter 6 mm) and cooled Active matrix layers were prepared by cutting the obtained rod into segments of 3.10 mm. A "sandwich" composition was then prepared by glueing inactive "lag layers" on both ends of the active layer, using PEG 1000 as glue, the lag layers having the same diameter of 6 mm and a length of 1.5 mm.

The composition of lag layer matrix was: 40% dextrin, 45% PEG 35,000, 15% PEG 400 monostearat, and the lag layer was prepared as described for the active layer.

After glueing, the three layers together, auxiliary rods of PEG 1500, diameter 6 mm, were glued on both ends of the "sandwich" and the whole unit was coated by dipping three times in 20% F 30 Estane soluted in tetrahydrofuran. After drying of the coating, the auxiliary rods were removed about 0.5 mm over the lag layers, the composition was placed in an oven, 40° C. The finished composition was open in both ends, consisting of an active middle layer containing 200 IE insulin, and lag layers of 1.5 mm in the ends, adjusted to erode in vitro over a period of 3 hours.

The composition was given orally to mini pigs, 25 kg body weight, in the fasting state, together with 200 ml of plain water. Venous blood samples were drawn after 1, 2, 3, 3½, 4, 5, 6, 7 and 9 hours, serum concentrations of blood glucose were measured using the method of Bannauch et al. (1975). The following results have been obtained:

TABLE 7

| Time (hours) | Composition A | | Composition B | |
|---|---|---|---|---|
| | Post-oral dose/serum glucose mmol/l | | | |
| | Pig 1 | Pig 2 | Pig 3 | Pig 4 |
| 1 | 3.2 | 3.3 | 2.9 | 3.2 |
| 2 | 3.5 | 3.6 | 3.1 | 3.5 |
| 3 | 3.4 | 3.6 | 2.8 | 3.4 |
| 3½ | 2.7 | 2.5 | 1.9 | 2.3 |
| 4 | 1.4 | 1.2 | 1.6 | 1.6 |
| 5 | 1.6 | 0.7 | 1.5 | 1.1 |
| 6 | 1.2 | 1.3 | 1.2 | 1.0 |
| 7 | 1.6 | 1.3 | 1.8 | 1.1 |
| 9 | 1.1 | 1.1 | 1.5 | 1.5 |

We claim:

1. A multi-layered article for controlled, pulsatile delivery of one or more active substances into an aqueous phase, comprising:
   at least one first layer comprising an active substance,
   at least one second layer different from said first layer, said second layer comprising said same active substance or a different active substance substantially homogeneously dispersed in a matrix, said matrix comprising a crystalline polymer and a non-ionic surface active agent, the melting point of said non-ionic surface active agent being lower than the melting point of said crystalline polymer, said non-ionic surface active agent being dispersed in said crystalline polymer in an amount of up to about 50% by weight, relative to the combined weight of said crystalline polymer and said non-ionic surface active agent, said non-ionic surface active agent comprising a domain which is compatible with said crystalline polymer and a domain which is substantially lipophilic, said amount of said non-ionic surface active agent being sufficient to effect repair of the surface of said second layer during exposure to said aqueous phase, and optionally, one or more layers comprising said matrix free of active substance;

wherein said first and second layers are configured so that at least one of said second layers is exposed to said aqueous phase before at least one remote first layer is exposed to said aqueous phase, said at least one second layer having a sufficient thickness to prevent exposure of said at least one remote first layer to said aqueous phase for at least about 15 minutes after exposure of said at least one second layer to said aqueous phase;

whereby each said second layer of said article erodes and releases said active substance therein at a substantially constant and controlled rate predominantly at said surface of said layer exposed to said aqueous phase; and wherein said active substance in each said first layer is released into said aqueous phase in a pulse and, for each remote first layer, after a selected time interval.

2. The article according to claim 1 wherein at least one of said first and second layers additionally comprises a filler.

3. The article according to claim 1 wherein said first layer comprises a filler and wherein said active substance is substantially homogeneously dispersed in said filler.

4. The article according to claim 1 wherein said non-ionic surface active agent comprises a water dispersible non-ionic surface active agent.

5. The article according to claim 1 wherein said non-ionic surface active agent comprises a water soluble non-ionic surface active agent.

6. The article according to claim 1, comprising a coating having an opening exposing at least one of said first and second layers to said aqueous phase.

7. The article according to clam 1, wherein each said second layer erodes at a substantially pH-independent rate.

8. The article according to claim 1, wherein said cyrstalline polymer is polyethylene glycol.

9. The article according to claim 8, wherein said polyethylene glycol has a molecular weight between about 20,000 daltons and about 500,000 daltons.

10. The article according to claim 9, wherein said polyethylene glycol has a molecular weight between about 20,000 daltons and about 300,000 daltons.

11. The article according to claim 10, wherein said polyethylene glycol has a molecular weight of about 35,000 daltons.

12. The article according to claim 1, wherein at least one of said first and second layers additionally comprises a filler, said filler being selected from said group consisting of diluents, binders, lubricants, disintegrants, coloring agents and dye migration inhibitors.

13. The article according to claim 2, wherein said first layer additionally comprises a polyethylene glycol having a molecular weight of between about 1,000 daltons and about 20,000 daltons.

14. The article according to claim 1, wherein said non-ionic surface active agent comprises a non-ionic surface active agent having at least one of a fatty acid ester and a fatty alcohol ether.

15. The article according to claim 14, wherein said fatty acid or fatty alcohol has a carbon chain of between 12 and 24 carbon atoms.

16. The article according to claim 14, wherein said non-ionic surface active agent is selected from the group consisting of an ester of palmitic acid, an ester of stearic acid, an ether of palmityl alcohol, an ether of stearyl alcohol, an ether of cetyl alcohol, an ether of cetostearyl alcohol, an ether of a wool alcohol and combinations thereof.

17. The article according to claim 1, wherein said non-ionic surface active agent is selected from the group consisting of a polyglycol ester, a polyglycol ether, a sugar ester, a sugar ether and combinations thereof.

18. The article according to claim 17, wherein said non-ionic surface active agent is selected from the group consisting of a polyethylene glycol ester, a polyethylene glycol ether, a sorbitan ester, a sorbitan ether and combinations thereof.

19. The article according to claim 18, wherein said non-ionic surface active agent comprises a polyethylene glycol stearate ester.

20. The article according to claim 19, wherein said non-ionic surface active agent comprises a polyethylene glycol monostearate, including polyethylene glycol 400 monostearate.

21. The article according to claim 1, wherein said non-ionic surface active agent is a non-ionic surface active agent having an HLB value of between about 5 and about 16.

22. The article according to claim 1, having the shape of a substantially cylindrical rod, said rod having two ends with respect to a longitudinal axis between said ends of said rod, wherein said first and second layers are arranged in a manner substantially transverse to said axis, and further comprising a coating substantially surrounding said rod and defining an opening adjacent at least one of said ends of said rod.

23. The article according to claim 22, wherein said coating comprises:

a matrix comprising a substantially water soluble polyethylene glycol and a non-ionic surface active agent, said transversely arranged first and second layers being erodible in said aqueous phase at particular rates and said coating being erodible in said aqueous phase at a second rate, said second rate being slower than either of said particular rates, whereby erosion of said article occurs at a substantially constant area defined by said opening and whereby said coating is eroded substantially after said first and second layers are eroded.

24. The article according to claim 22, wherein said coating comprises a polyethylene glycol having a molecular weight of between about 10,000 daltons and about 500,000 daltons.

25. The article according to claim 22, wherein said coating is self-supporting and is insoluble in and impermeable to said aqueous phase for a predetermined period of time.

26. The article according to claim 1 comprising a plurality of active substances.

27. The article according to claim 1, wherein said second and said first layers comprise different active substances.

28. The article according to claim 1, wherein said second and said first layers comprise the same active substance.

29. The article according to claim 1, in the form of a tablet having an outer layer and an inner core, wherein said outer layer comprises said first layer and said inner core comprises said second layer of said tablet.

30. The article according to claim 29 comprising a plurality of active substances.

31. The article according to claim 29, wherein said second and said first layers comprise different active substances.

32. The article according to claim 29, wherein said second and said first layers comprise the same active substance.

33. The article according to claim 1, in the form of a tablet having an outer layer, an intermediate layer and an inner core wherein said outer layer and said inner core comprise said first layer and wherein said intermediate layer is disposed between said outer layer and said inner core.

34. The article according to claim 1, having an enteric coating.

35. The article according to claim 34, wherein said enteric coating comprises a material selected from the group consisting of cellulose acetate phthalate, hydroxypropyl methylcellulose phthalate, methacrylic acid-methacrylic acid ester copolymers, and combinations thereof.

36. The article according to claim 35, further comprising an enteric coating, said enteric coating comprising at least one active substance.

* * * * *

UNITED STATES PATENT AND TRADEMARK OFFICE
CERTIFICATE OF CORRECTION

PATENT NO. : 5,213,808
DATED : May 25, 1993
INVENTOR(S) : Bar-Shalom, et. al.

It is certified that error appears in the above-indentified patent and that said Letters Patent is hereby corrected as shown below:

On the Title page, item [75], inventor: change "Kindt-Larsen" to -- Ture Kindt-Larsen--.

Column 30, claim 21, line 2, change "anon-ionic" to --a non-ionic--.

Signed and Sealed this

Seventeenth Day of May, 1994

Attest:

BRUCE LEHMAN

*Attesting Officer*  *Commissioner of Patents and Trademarks*

UNITED STATES PATENT AND TRADEMARK OFFICE
CERTIFICATE OF CORRECTION

PATENT NO. : 5,213,808
DATED : May 25, 1993
INVENTOR(S) : Daniel BAR-SHALOM et al.

It is certified that error appears in the above-indentified patent and that said Letters Patent is hereby corrected as shown below:

On the title page:

Item: [73], contains a typographical error wherein "Buhk Meditec A/A" should read --Bukh Meditec A/S--.

Signed and Sealed this

Twenty-ninth Day of August, 1995

Attest:

BRUCE LEHMAN

*Attesting Officer*     *Commissioner of Patents and Trademarks*